United States Patent
Kusuma et al.

(10) Patent No.: US 10,665,335 B2
(45) Date of Patent: May 26, 2020

(54) INTEGRATED SYSTEM AND METHOD FOR THE ACQUISITION, PROCESSING AND PRODUCTION OF HEALTH CARE RECORDS AND SERVICES

(71) Applicant: Symplast Acquisition, Inc., Plantation, FL (US)

(72) Inventors: Shashidhar Kusuma, Plantation, FL (US); Munish K. Batra, San Diego, CA (US); Bhupesh Vasisht, Voorhees, NJ (US)

(73) Assignee: SYMPLAST ACQUISITION, INC., Plantation, FL (US)

( * ) Notice: Subject to any disclaimer, the term of this patent is extended or adjusted under 35 U.S.C. 154(b) by 85 days.

(21) Appl. No.: 16/117,687

(22) Filed: Aug. 30, 2018

(65) Prior Publication Data

US 2018/0374564 A1    Dec. 27, 2018

Related U.S. Application Data

(62) Division of application No. 14/747,452, filed on Jun. 23, 2015, now Pat. No. 10,089,438.

(60) Provisional application No. 62/017,873, filed on Jun. 27, 2014.

(51) Int. Cl.
| | | |
|---|---|---|
| *H04L 29/08* | (2006.01) | |
| *G16H 10/60* | (2018.01) | |
| *G16H 15/00* | (2018.01) | |
| *G16H 30/40* | (2018.01) | |
| *G06F 19/00* | (2018.01) | |

(52) U.S. Cl.
CPC .............. *G16H 10/60* (2018.01); *G06F 19/00* (2013.01); *G16H 15/00* (2018.01); *G16H 30/40* (2018.01); *H04L 67/10* (2013.01); *H04L 67/18* (2013.01); *H04L 67/2823* (2013.01); *H04L 67/32* (2013.01)

(58) Field of Classification Search
CPC ........ G16H 10/60; G16H 15/00; G16H 30/40; G06F 19/00; H04L 67/10; H04L 67/18; H04L 67/2823; H04L 67/32
USPC .......................................................... 726/2
See application file for complete search history.

(56) References Cited

U.S. PATENT DOCUMENTS

| | | | | |
|---|---|---|---|---|
| 2008/0082980 A1* | 4/2008 | Nessland | ............... | G06Q 10/02 718/104 |
| 2009/0198728 A1* | 8/2009 | Davia | .................. | G06Q 10/109 |
| 2013/0268740 A1* | 10/2013 | Holt | ........................ | G06F 21/00 711/163 |

* cited by examiner

*Primary Examiner* — Michael S McNally
(74) *Attorney, Agent, or Firm* — Robert C. Kain, Jr.

(57) ABSTRACT

The highly secure method and system acquires, processes and produces health care (HC) data and service records from multiple local devices, notwithstanding different operating systems (OS) in such devices, and all accessed and controlled by a cloud computing network. Devices have memories, displays, keypads, cameras and microphones. The system operates on acquired data including image, keypad-text, audio, and speech-converted-to text data generated by respective devices. The method downloads commands to devices (notwithstanding different OS) which delete-acquired-data upon a request to save (upload) data to the cloud computing network. Further data security includes a disable-print-screen command prohibiting local storage of stored acquired data into local devices. The method and system also produces a customized surgical schedule by (a) obtaining the GPS location of a local device (b) filtering out the non-surgical appointments from the complete appointment schedule of the HC professional; and (c) displaying only surgical appointments.

5 Claims, 40 Drawing Sheets

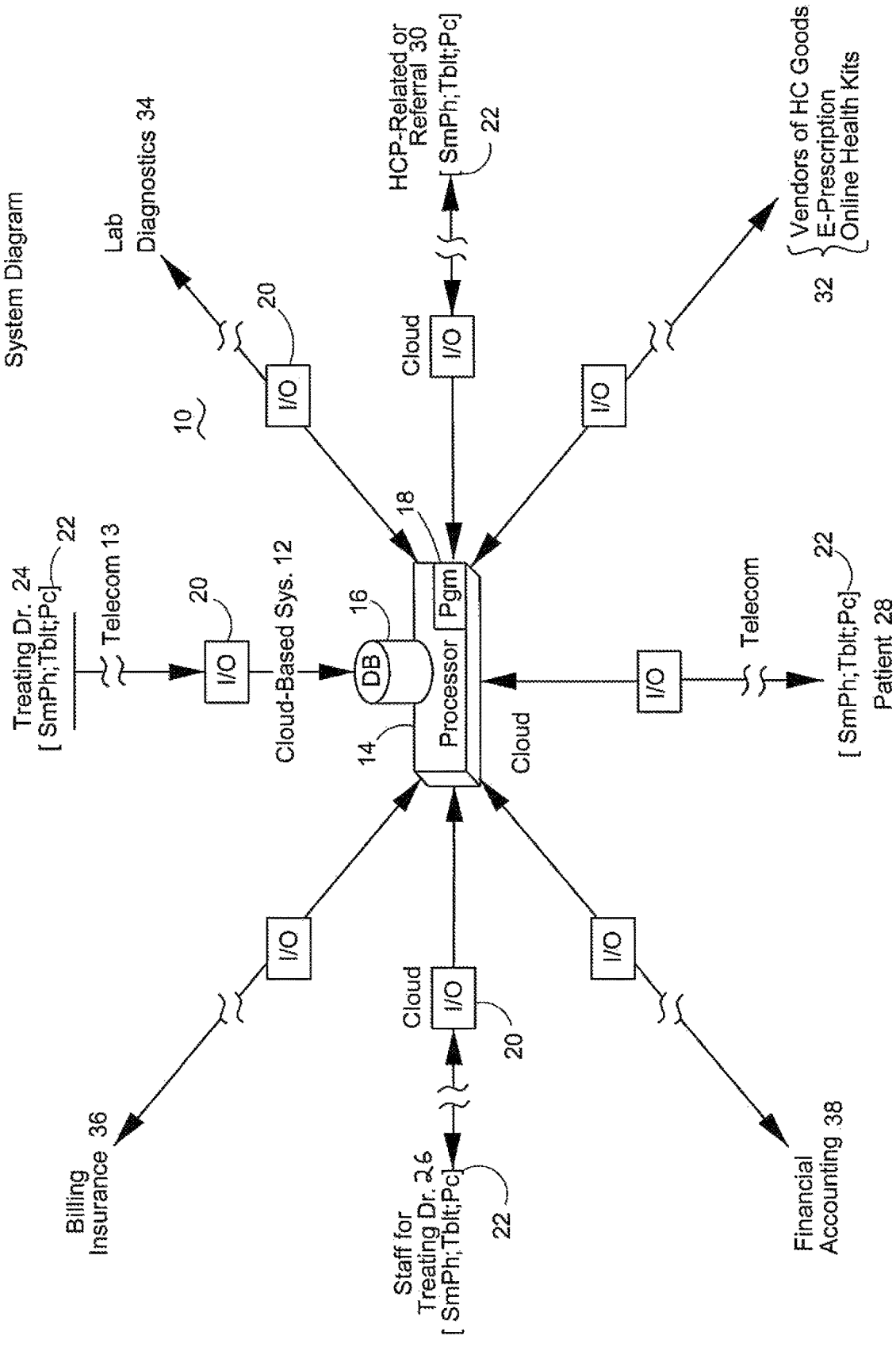

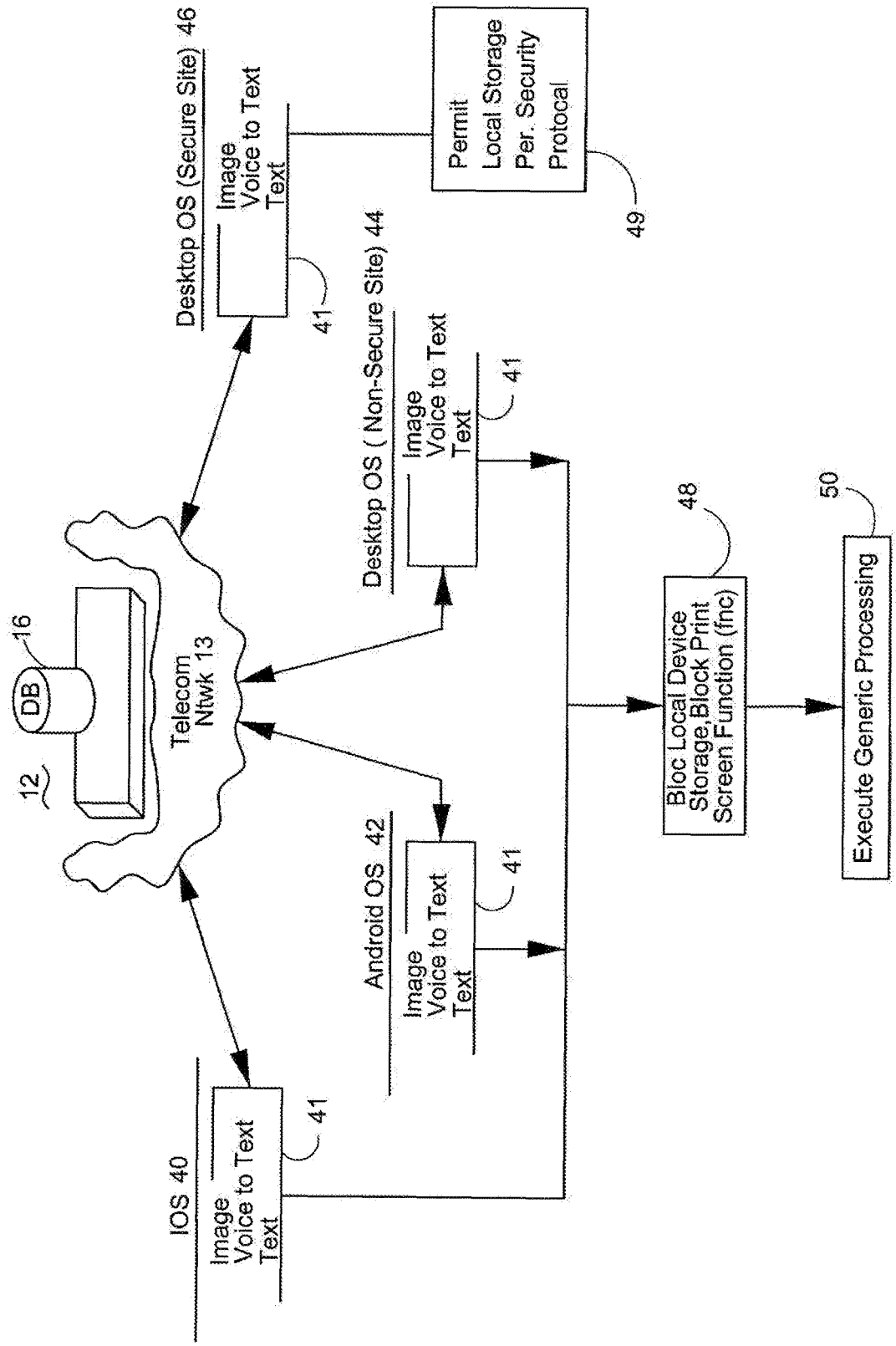

FIG.3A

```
        ( Generic Agnostic Acquisition and )
        (      Processing Flow Chart       ) — 52
                        │
                        ▼
        ┌─────────────────────────────────┐
        │ Request (RQT) "Save Image" from │
        │   Local Device to System (Sys.) │ — 54
        └─────────────────────────────────┘
                        │
                        ▼
        ┌─────────────────────────────────┐
        │  Sys Command (cmd) when upload  │
        │   Image; Delete Image from Local│ — 56
        │          Memory (mem)           │
        └─────────────────────────────────┘
                        │
                        ▼
        ┌─────────────────────────────────┐
        │ Optional (Opt) - cmd prohibit   │ — 58
        │        Screen Print (prn)       │
        └─────────────────────────────────┘
                        │
                        ▼
        ┌─────────────────────────────────┐
        │ Local Device Uploads Image to   │ — 60
        │    Sys.; Sys saves Image in DB  │
        └─────────────────────────────────┘
                        │
                        ▼
              ( Non-Sequential Event ) — 62
                        │
                        ▼
        ┌─────────────────────────────────┐
        │ RQT from Local Device to Sys.   │ — 64
        │    "Save Audio Record" (a-rcd)  │
        └─────────────────────────────────┘
                        │
                        ▼
        ┌─────────────────────────────────┐
        │  Sys. cmd; when Upload a-rcd    │ — 66
        │   Delete a-rcd from Device Mem. │
        └─────────────────────────────────┘
                        │
                        ▼
        ┌─────────────────────────────────┐
        │ Device Uploads a-rcd to Sys,    │ — 68
        │        then Sys. stores         │
        └─────────────────────────────────┘
                        │
                        ▼
              ( Non - Sequential ) — 70
                        │
                        ▼
        ┌─────────────────────────────────┐      ┌──────────────┐
        │ RQT from Local Device to Sys. - │ ───▶ │ Jump to      │ — 74
        │ Save Text Data created by Speech│ — 72 │   Step 76    │
        │ to Text Generator (V-Text Data) │      └──────────────┘
        └─────────────────────────────────┘
```

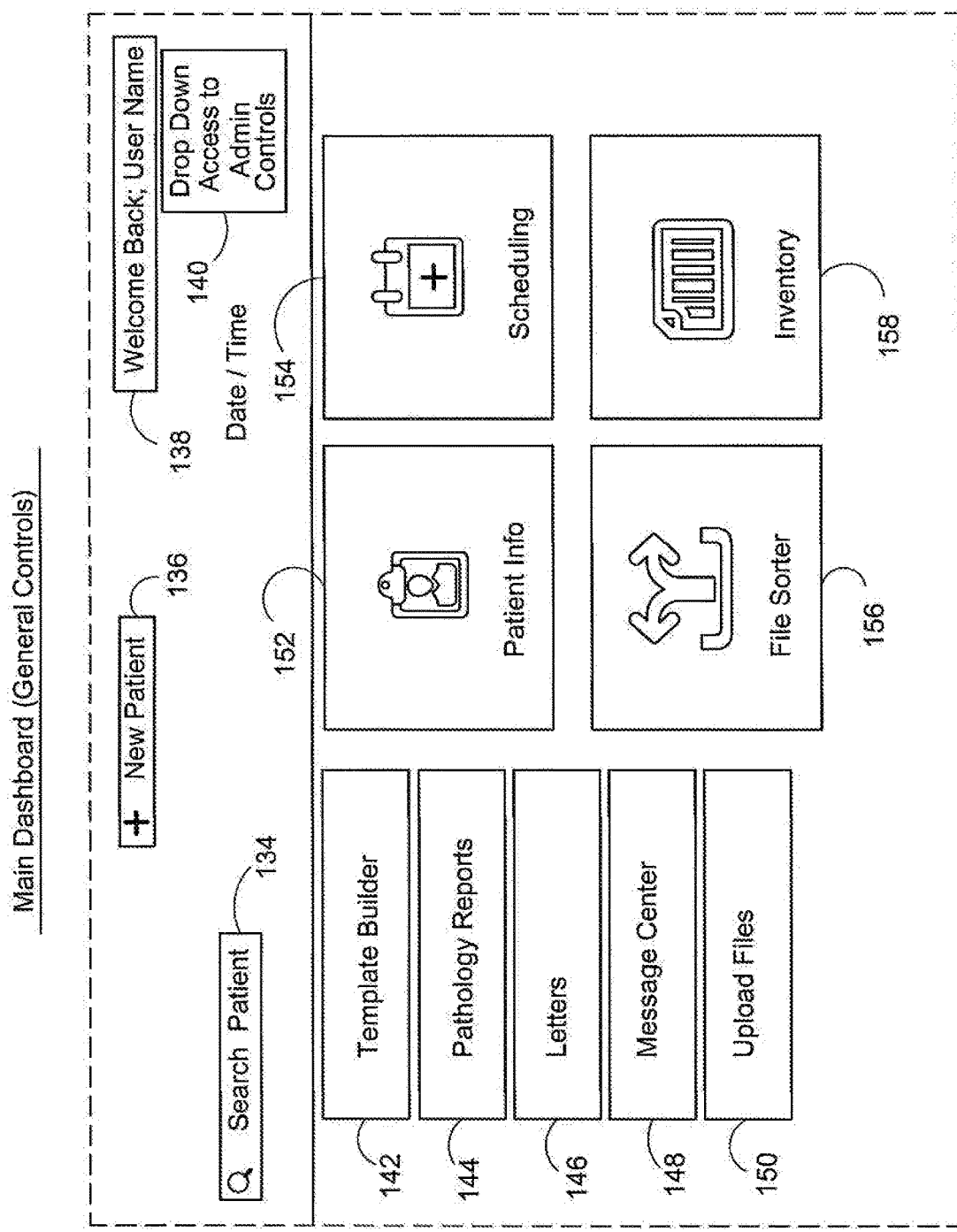

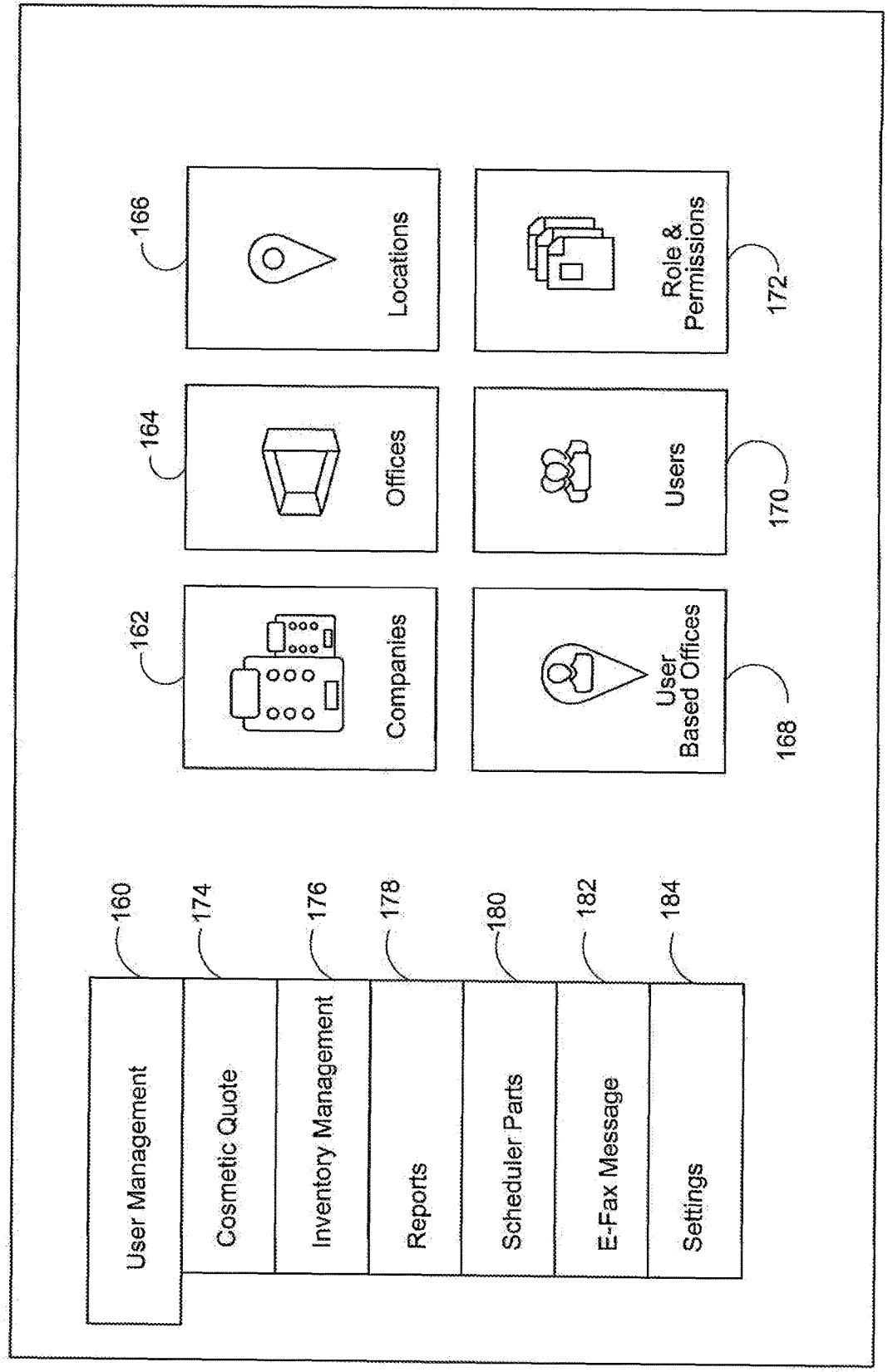

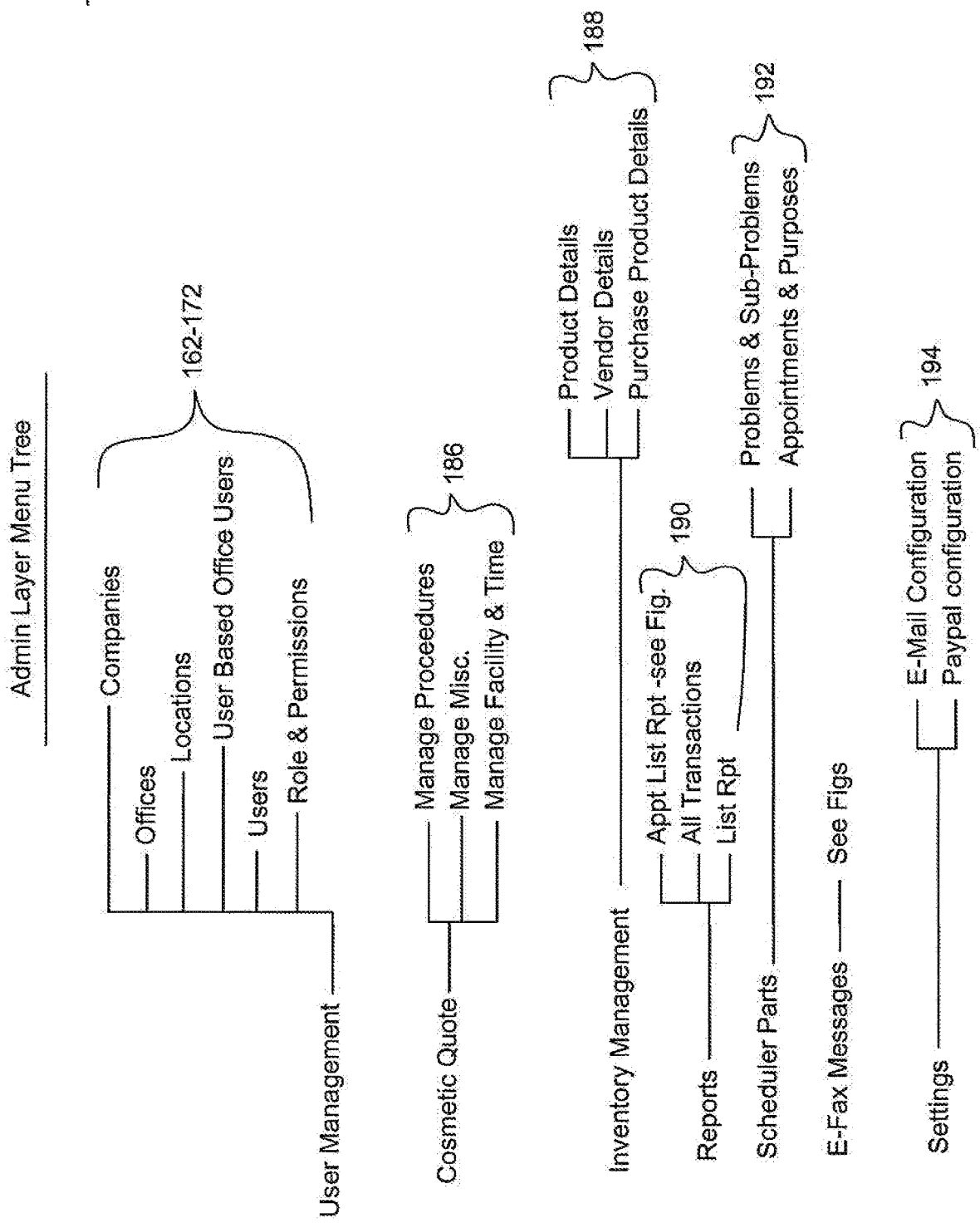

FIG.9A

Sell Product

Inventory A (Admin)

Date: 5/11/2015:4:17:50 PM

Remove Items

☑ For Patient  273,04,  — 196, 202, 204, 206 fnc 198  ✕

| Product Name | In-Stock | Quantity | Rate($) | Disc($) | Amount($) |
|---|---|---|---|---|---|
| Cream La Mer | 26 | 1 | 100 | 0 | 100.00 |

Total Amount  100.00

Global Discount: $ [    ]    Total Discount Amount: $ 0.00

Total Amount: $100.00    Total Amount After Discount: $ 100.00

[Sell]   [Internal Use]   [Cancel]   [+Add More]

Inventory B (Admin)

Home  Inventory  Sell Product

| Barcode | Product Type | Product Name | In-Stock Quantity | Add to Cart |
|---|---|---|---|---|
| 735081496 | Cosmetic | Crem La Mer | 26 | ✓ |
| 670559967 | | Arnica Forte | 1 | ☐ |
| 428203441 | | Biocornium | 3 | ☐ |
| 143127767 | | Hydrate | 3 | ☐ |
| 13540733375 | | Exforderm | 3 | ☐ |

Add to Cart

216 — Search Product
218 — Q fnc 220

FIG.11

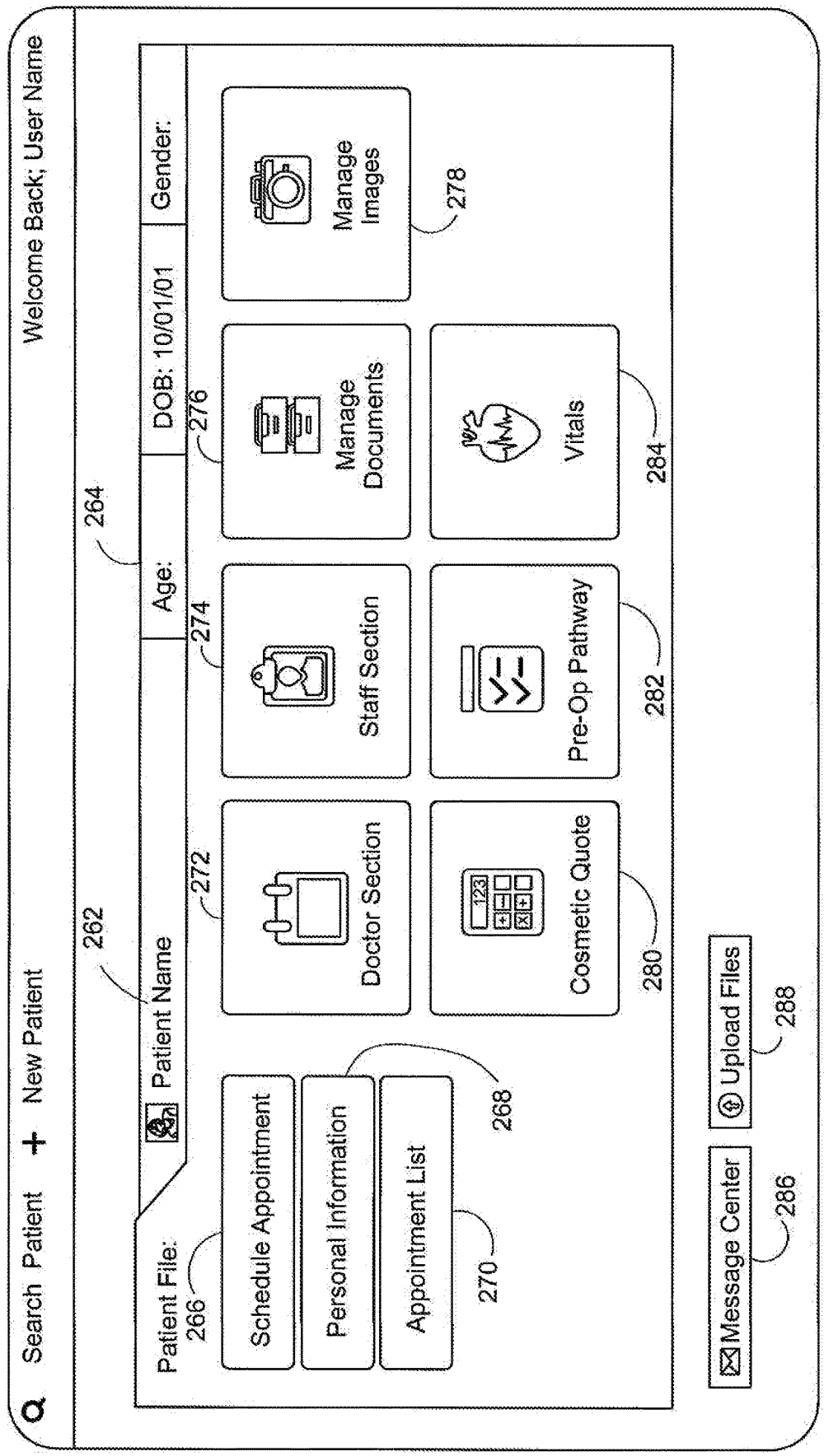

FIG.14A

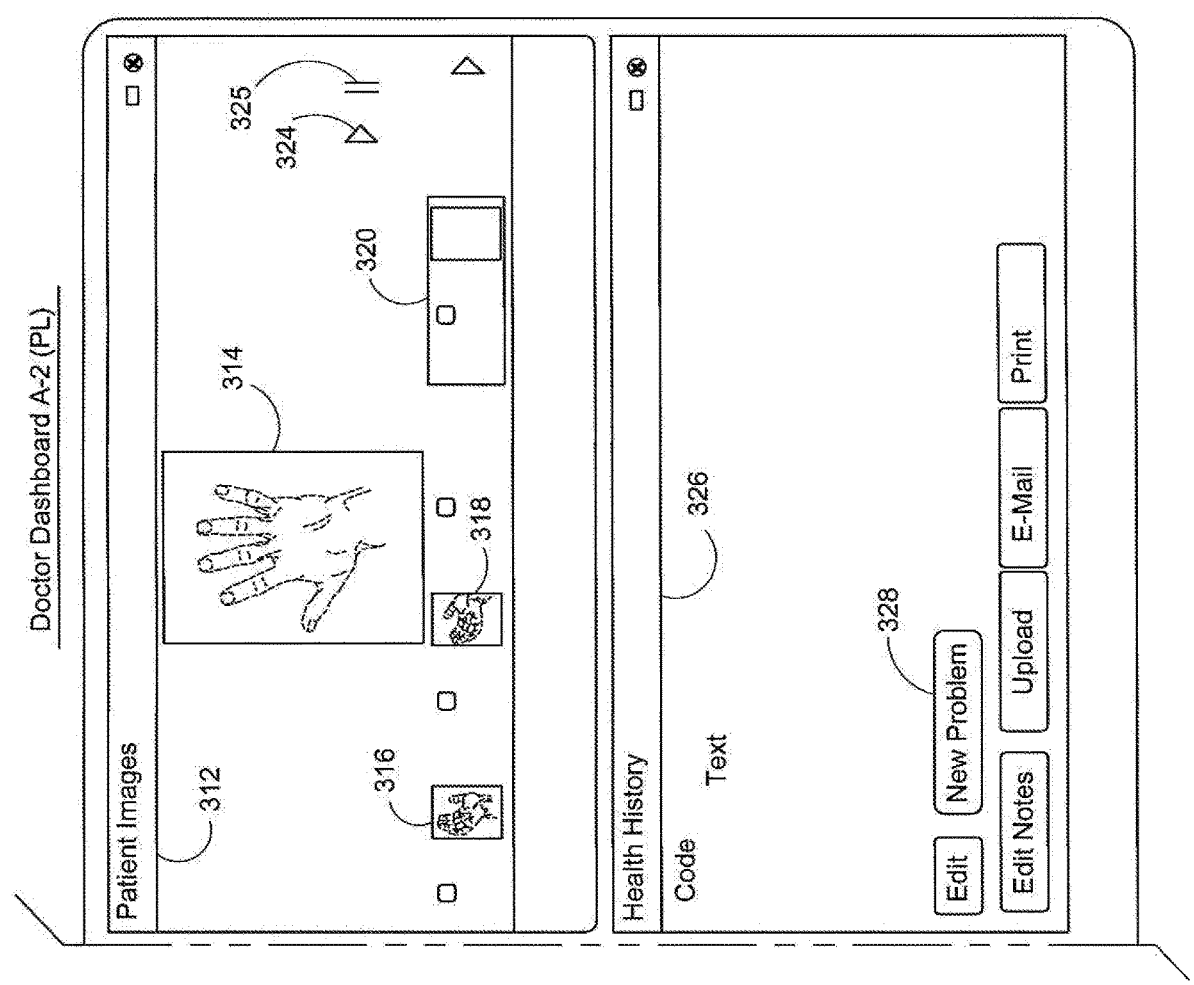

FIG. 20

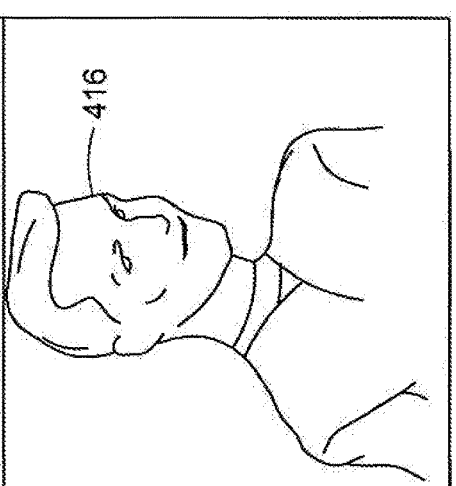

FIG.22A

Cosmetic Quote C-1 (PL)

Summary 426

Professional / Surgery Fees

| # | Procedure | Time(hr) | Actual Cost($) | Discount($) % | Value($) |
|---|---|---|---|---|---|
| 1 | Abdominoplasty + Flank Liposuction | ☐ | $6,250.00 | | |
| 2 | Upper or Lower Blepharoplasty (Eyelids) | ☐ | $3,100.00 | | |
| | Total: | | $9,350 | | 0.00 |

Anesthesia Fees

| Facility | Price($) | Time(hr) |
|---|---|---|
| Choose Facility ◄► | $6,250.00 | ☐ |
| Choose Facility ◄► | $3,100.00 | ☐ |
| | $9,350 | |

Miscellaneous Fees

| # | Procedure Name | Fees($) | |
|---|---|---|---|
| 1 | Garment | 0.00 | Please enter amount |
| # | Please enter miscellaneous | | Edit / Delete |
| | | | Add |

Total Amount: $9,350.00          Total Discount Amount: $0.00

[Back]

FIG.22B

Cosmetic Quote C-2 (PL)

| Fees($) | | |
|---|---|---|
| | | 0.00 |

Facility & Time — 438

| Facility | Time(hr) | Fees($) |
|---|---|---|
| Choose Facility ◄► | ☐ | |
| Choose Facility ◄► | ☐ | 0.00 |

— 432

⎫
Global Surgery Fees: [Please enter amount]
Global Anesthesia Fees: [Please enter amount]  ⎬ 444
Global Facility & Time Fees: [Please enter amount]
Global Discount: [Please enter amount]
⎭

Total Amount after Discount: $9,350.00 — 446

[Done]

FIG.23

Cosmetic Quote D (PL)

Patient Center  Document Management  Cosmetic Document  Cosmetic Payment List

Patient File: | 👤 Patient Name ID  J. Gallo (ID#273)   Age: 36   DOB: 04/13/1979   Gender: Male

448

| Total Amount | Total Paid Amount | Completed | Payment |
|---|---|---|---|
| 10200 | 1000 | No | Online  Cash |
| 10000 | 1000 | No | Online  Cash |

450  452

✉ Message Center   ⊕ Upload Files

FIG.24

Pre-Op Pathway (PL)

Pre-Op Pathways — 454

Maria:_Pre-Operative Checklist ▽△ | Save Pre-Op Template — 456 | Cancel

▽ Pre-Operative Checklist

Patient Name | Patient Number | Surgery | Facility

Surgery_Date | Time | Allergies ○Yes ○No | Diabetic ○Yes ○No | Blood_Thinners ○Yes ○No Anesthesia

Vitals B (PL)

Patient Vitals — 462

Height (in) [172]　Weight (lb) [156]　BP [45]　BMI [3.7] — 464

☑ Medication Reconciliation performed
☑ Inquiry reguarding tobacco use done
☑ Advised on smoking and tobacco cessation programs
☑ Pt. specific education resources have been provided
☑ Pt. was sent reminder via their preferred contact method
☑ Summary complete and provided within 3 business days
☑ Care transitioned from another provider　Yes ○　No ○

— 466

[Save]　[Cancel]

FIG.27

Schedule Appointment (PL)

Schedule Appointment — 468

- Status: Pending
- Patient: Select Patient | Add New Patient
- Location: Plantation-IOS
- Start Date: 5/11/2015  6:30am
- Appointment Type: New Consult
- Problem: Select Problem
- Select Existing Insurance: No Record Found

470

- Confirmed: ○ No — 471
- Physician: ○ J. Rouzand
- End Date: 5/11/2015  7:00am  ☐ All Day
- Appointment Purpose: ○ Select Appointment Purp.
- Sub-Problem: No Record Found | Add New Problem
- Eligibility Status: Not Eligible

474

Notes: 472

☐ Recurrance

- Save & Exit — 476
- Save & Go to Patient — 478
- Exit — 480
- Go to Patient Dashboard — 482

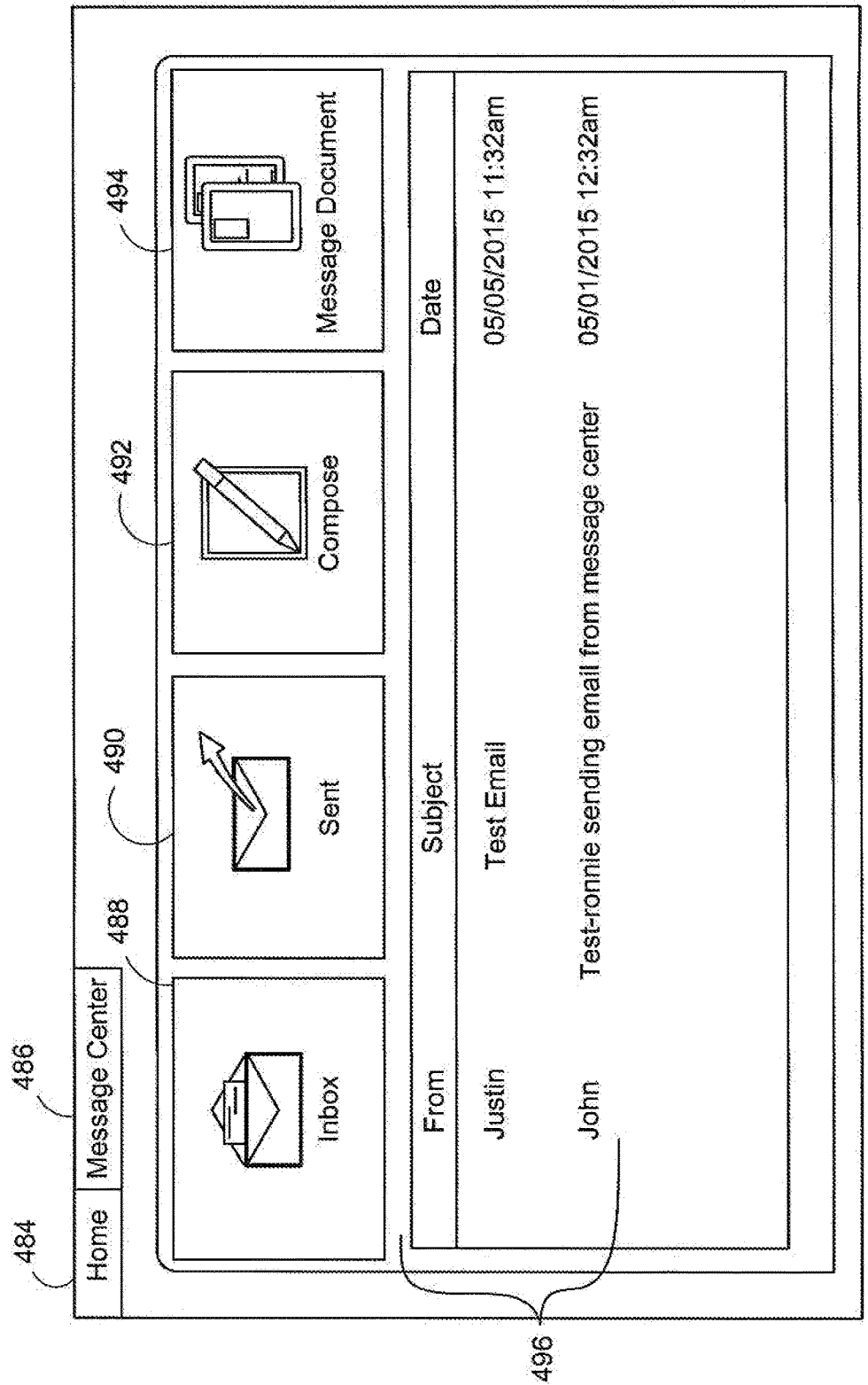

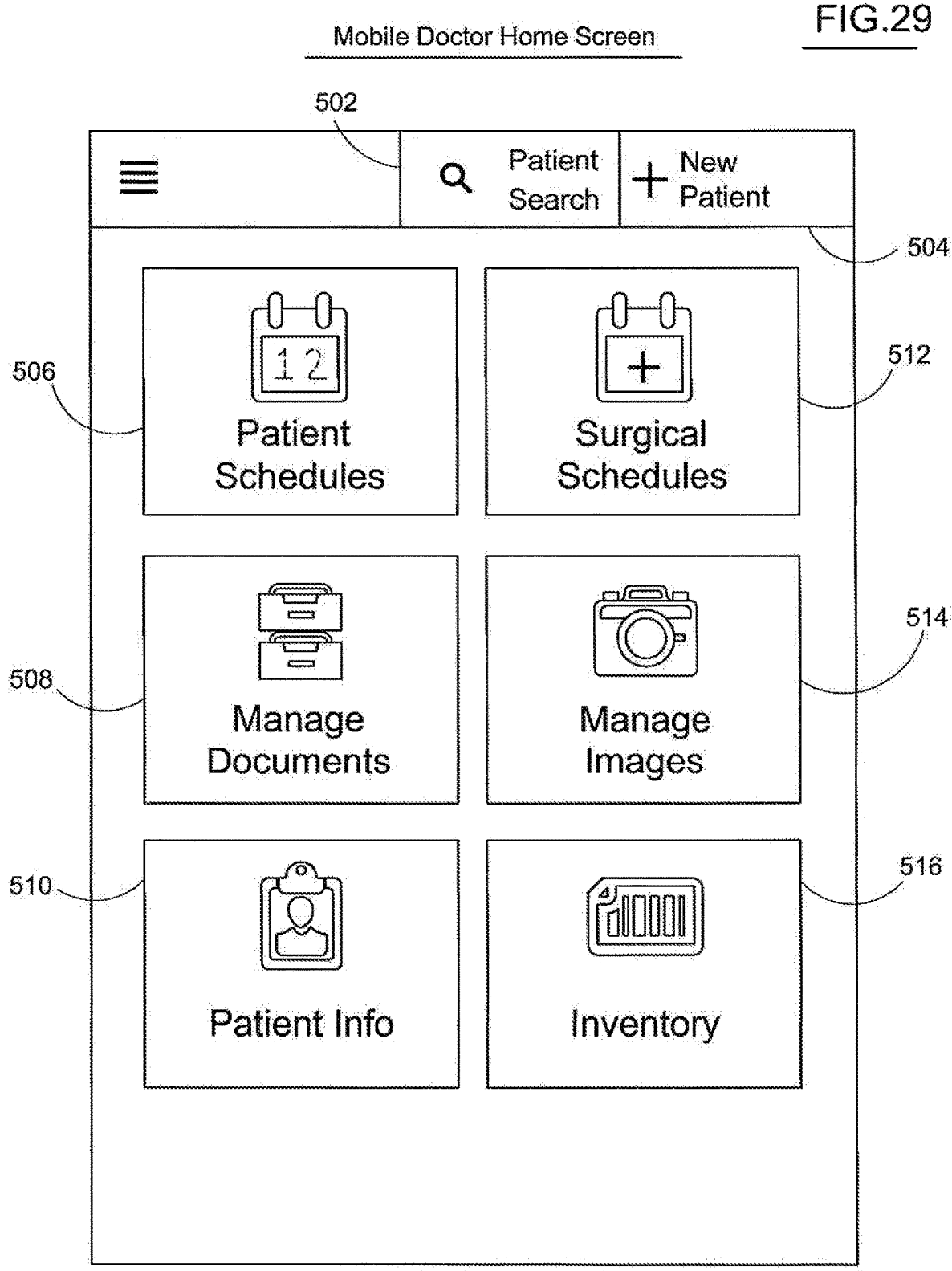

FIG. 31

INTEGRATED SYSTEM AND METHOD FOR THE ACQUISITION, PROCESSING AND PRODUCTION OF HEALTH CARE RECORDS AND SERVICES

This is a divisional patent application based upon and claiming the benefit of U.S. patent application Ser. No. 14/747,452, filed Jun. 23, 2015, now pending, which was a regular patent application based upon and claiming the priority of provisional patent application Ser. No. 62/017,873, filed Jun. 27, 2014, the contents of which is incorporated herein by reference thereto.

The present invention relates to a highly secure method for the acquisition, processing and production of healthcare data and service records implemented in a cloud computer network. In order to provide a seamless system which can accommodate a number of different devices such as desktop computers, Apple™ mobile devices (using IOS operating systems) and Android™ mobile devices (using an Android OS or operating system), the cloud based system is agnostic to the computer device coupled to the system via a telecommunications network. Additionally, with the use of Microsoft™ SQL database in the cloud-based healthcare data-service system, other computer database systems can be mapped to the inventive cloud-based healthcare data-service system by mapping the fields of the cloud-based healthcare data-service system database to the other computer system. For example, labs which generate electronic medical record lab data (EMR lab data) for a "lab patient" can upload the EMR lab data into the cloud-based healthcare data-service system after personnel at the health care provider (HCP) operating the data-service system matches the lab patient to the HCP patient in the data-service system. The upload of remaining EMR lab data is seamless if the fields match the data-service system database. The Abbreviations Table near the end of this patent specification contains several abbreviations used herein.

FIELD OF THE INVENTION

The present invention lies in the field of patient administration. The present disclosure relates to methods and systems for healthcare solutions, including a process and software for carrying out medical patient administration.

BACKGROUND

There is a need for a cloud-based healthcare data-service system which is input device agnostic, thereby permitting physicians and HCP staff to quickly access health care (HC) data for a particular patient, gather or obtain HC data from a patient (images, audio converted to text and keypad input text data), and store that HC data in a universally accessible cloud based system (assuming the inquiring party has system-established permissions to view and/or input or download the HC data for a particular patient).

Cloud computing is the current trend to reduce the need for on-site hardware and to increase the input and output of data useful in business applications. Cloud computing is the practice of using a network of remote servers hosted on the Internet to store, manage, and process data, rather than a local server or a personal computer. Further, cloud computing means storing and accessing data and programs over the Internet. Cloud computing is sometimes defined as the practice of storing regularly used computer data on multiple servers that can be accessed through the Internet

OBJECTS OF THE PRESENT INVENTION

It is an object of the present invention to provide a seamless data acquisition and data input system and method for HCPs, using any commonly available computer-based device (desktop computer, mobile smart phone or tablet) to input, process and upload HC data into a cloud-based healthcare data-service system.

It is another object of the present invention to maintain a high degree of security regarding the input and storage (or severely limited storage) of HC data on the local devices which are coupled to the cloud-based healthcare data-service system via telecommunications network(s) and the Internet. By severely limiting the storage of locally acquired HC data on the mobile devices, the HCPs using the system can be assured that the cloud-based healthcare data-service system keeps all HC data for a patient in a secure, single location.

SUMMARY OF THE INVENTION

The invention provides methods and systems for healthcare solutions that overcome the hereinafore-mentioned disadvantages of the heretofore-known devices and methods of this general type.

The comprehensive platform is configured for outpatient based surgical practices. It is a .NET based cloud application along with native IOS and Android™ and Google Glass™ and other data acquisition mobile applications that seamlessly integrate and interact with each other in real time. The mobile applications include four native apps (APPs) that include a HCP Provider app, a HCP Staff app, a Patient app, and a referring or related Physician app. The idea of the systems and methods of the invention is to generate one cloud-based healthcare data-service system database that can be utilized selectively by all involved parties to eliminate duplicity and inefficiency, to improve immediacy, and to promote transparency.

Several parts of the cloud-based healthcare data-service system platform (or cloud-based platform) are unique and are illustrated, for example, with screen shots. The apps create a very intuitive and efficient workflow that is completely configured by HCP surgeons for surgeons who understand the workflow intimately.

The cloud-based healthcare data-service system and method offers an "Information Technology In a Box" or "IT-in-a-box" concept to surgeons and HCPs. The system and method includes the following functions that are integrated in at the coding level to become the most comprehensive platform available. The complete healthcare IT solutions package for surgeons and HCPs includes the items in the following Table.

| Table Examples of IT Modules |
|---|
| Practice management |
| EMR (electronic medical records) |
| Inventory management |
| Billing and financial |
| Hosting and network support |
| General IT support for the office |
| Hardware installation and support |
| HIPPA compliance support |
| Marketing and website support and maintenance |
| Banking - Financial support |
| Image and document management |
| Unlimited storage on the cloud |

In essence, use of the cloud-based healthcare data-service system and associated programs and methods takes care of everything that is IT-related to a physician's office. Various advantages provided by the programs and methods are outlined throughout the specification. The inventive program and method allows for direct importation of HC faxed data into the system and uploading those documents into respective folders in appropriate patient charts all on a grid at one time.

A grid/chart is created for each day of all insurance claims and all of them are uploaded to a clearing house. With the advent of Google Glass™ and other mobile image acquisition systems (for example, GoPro™ cameras) (herein mobile camera systems or MCS), mobile camera systems are integrated into the cloud-based healthcare data-service system workflow to take and upload photos into the mobile APP or the HC office based software application directly. Further the HCP can retrieve the photos and documents directly from the application. Potentially, the cloud-based healthcare data-service system can download the captured images into the Google Glass™ display worn by the HCP.

A four-tile or quad-segments screen design of the EMR note section is disclosed and illustrated herein. Each of the tiles or quad segments are active tiles that can be populated with different HC data points, either acquired at the time of viewing or downloaded from the cloud-based healthcare data-service system.

The inventory module and workflow of the inventory module are efficient.

The template builder module provides a preformatted template that is integrated into, for example, Dragon Dictation™ (voice converted to text), as another active control. Also, the program provides the ability to directly upload any image that is taken on the IOS device into the EMR note template. In particular, the doctor can create a custom template for any problem, for example, treatment of a mole on the face. The physician can take a photo from the IOS device and directly upload it into the patient note through the custom template. The physician can use the template that he/she created for the mole that is preformatted and prefilled, but also can dictate the exam and plan of action at the end of the custom template. The four provided apps (including the Provider app, the Staff app, the Patient app and the Referring or Related Doctor app) in real time seamlessly integrate the cloud version of the cloud-based healthcare data-service system, method and program.

The visual layout of the staff view and doctor view sections of the EMR allow for better workflow as being intuitive to the way a surgeon works. The system, method and program allows the template builder to all aspects of the software including: use by the HCP staff to create staff-related templates, use by the surgeon for creating patient notes, and use by the HCP administrative staff to perform all of the ancillary paperwork. For example, a doctor can create a custom template for a lesion of the face, the HCP staff can create a follow-up note or other instructions for patients for post-operative care or the HCP administrative staff can generate a template for school time off notes or time off for work notes or for insurance paper work. The template builder is coded into each of the different sections of the system and is accessible in all of these different parts of the program.

The system and method uses a native Patient app accessible by the HC patient on his or her mobile phone or desktop.

Each of the apps (whether an HCP APP or a Patient APP) are secure and protected as being HIPPA compliant. The apps allow patients to communicate with the physician's office, to be connected, to have access to permissible medical documents, images, invoice, billing, and other features that will make this a tool that improves communication and access between a surgeon and a patient.

The referring or related doctor app will be given to referring or related physicians' offices that can, in real time, have access to the patient's HC information and also to send over and upload information into the cloud-based healthcare data-service system. This eliminates the faxing and scanning and other forms of inefficient communication between the treating doctor and the related doctor or referring doctor and allows access to the HC information instantaneously. Using the referring/related doctor app, the physician's office can upload any necessary documents, paperwork, information, and/or images into the HCP system database that can be viewed and accessed by the consulting physician in real time and vice versa.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

BRIEF DESCRIPTION OF THE DRAWINGS

The accompanying figures, where like reference numerals refer to identical or functionally similar elements throughout the separate views, which together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which:

FIG. 1 diagrammatically illustrates a System Diagram showing the interconnection between the cloud-based processor and data base and the numerous input and output devices for the patient data and health care data.

FIG. 2 diagrammatically illustrates a Agnostic Acquisition and Processing System.

FIGS. 3A and 3B diagrammatically illustrate a Generic Agnostic Acquisition and Processing Flow Chart.

FIGS. 4 and 5 are discussed later in the specification in conjunction with the Doctor Mobile Schedule Module(s), FIG. 32.

FIG. 5 diagrammatically illustrates a Surgical Scheduling (Central Processing) flow chart (see discussion of FIG. 32).

FIG. 6 diagrammatically illustrates a Main Dashboard for General Controls.

FIG. 7 diagrammatically illustrates an Admin (User Management) input and data screen control.

FIG. 8 diagrammatically illustrates an Admin Layer Menu Tree.

FIGS. 9A and 9B diagrammatically illustrate an Inventory A (Admin) screen and an Inventory B (Admin) screen.

FIG. 10 diagrammatically illustrates a Calendar Schedule (Admin) screen.

FIG. 11 diagrammatically illustrates a File Sorter (Admin Layer) screen (discussed after FIG. 12).

FIG. 13 diagrammatically illustrates a Patient Layer (PL).

FIGS. 14A and 14B diagrammatically illustrate a Doctor Dashboard A-1 (Patient Layer or "PL") and a continuation of the Doctor Dashboard A-2 (PL) as FIG. 14B. In practice, screens 14A and 14B are side-by-side. FIGS. 14A and B, 15 and 16 discussed in connection with the Doctor Views Section after FIGS. 17, 25 and 26.

FIGS. 18 and 19 are discussed in the Image Management Section.

FIG. 19 diagrammatically illustrates an Image Manager Section (PL)(see Image Management Section).

FIGS. 20, 21, 22A, 22B and 23 diagrammatically illustrate Cosmetic Quote A (PL) screen, Cosmetic Quote B (PL) screen, Cosmetic Quote C (PL) screen, and Cosmetic Quote D (PL) screen (see Cosmetic Quote Section).

FIG. 24 diagrammatically illustrates a Pre-OP Pathway (PL)(see Pre-Op Pathway Section).

FIGS. 25 and 26 diagrammatically illustrate screens for Vitals A (PL) and Vitals B (PL)(see Meaningful Use—Vitals Section which precedes FIGS. 14A and B).

FIG. 27 diagrammatically illustrates a Schedule Appointment (PL)(see Schedule Appointment Section).

FIG. 28 diagrammatically illustrates a Message Center (PL).

FIG. 29 diagrammatically illustrates a Mobile Doctor Home Screen (see Doctor or HCP Provider App Section).

FIG. 31 diagrammatically illustrates a Mobile Doctor or HCP Schedule (see Doctor or HCP Provider App Section).

DETAILED DESCRIPTION OF THE INVENTION

Figure 3B:
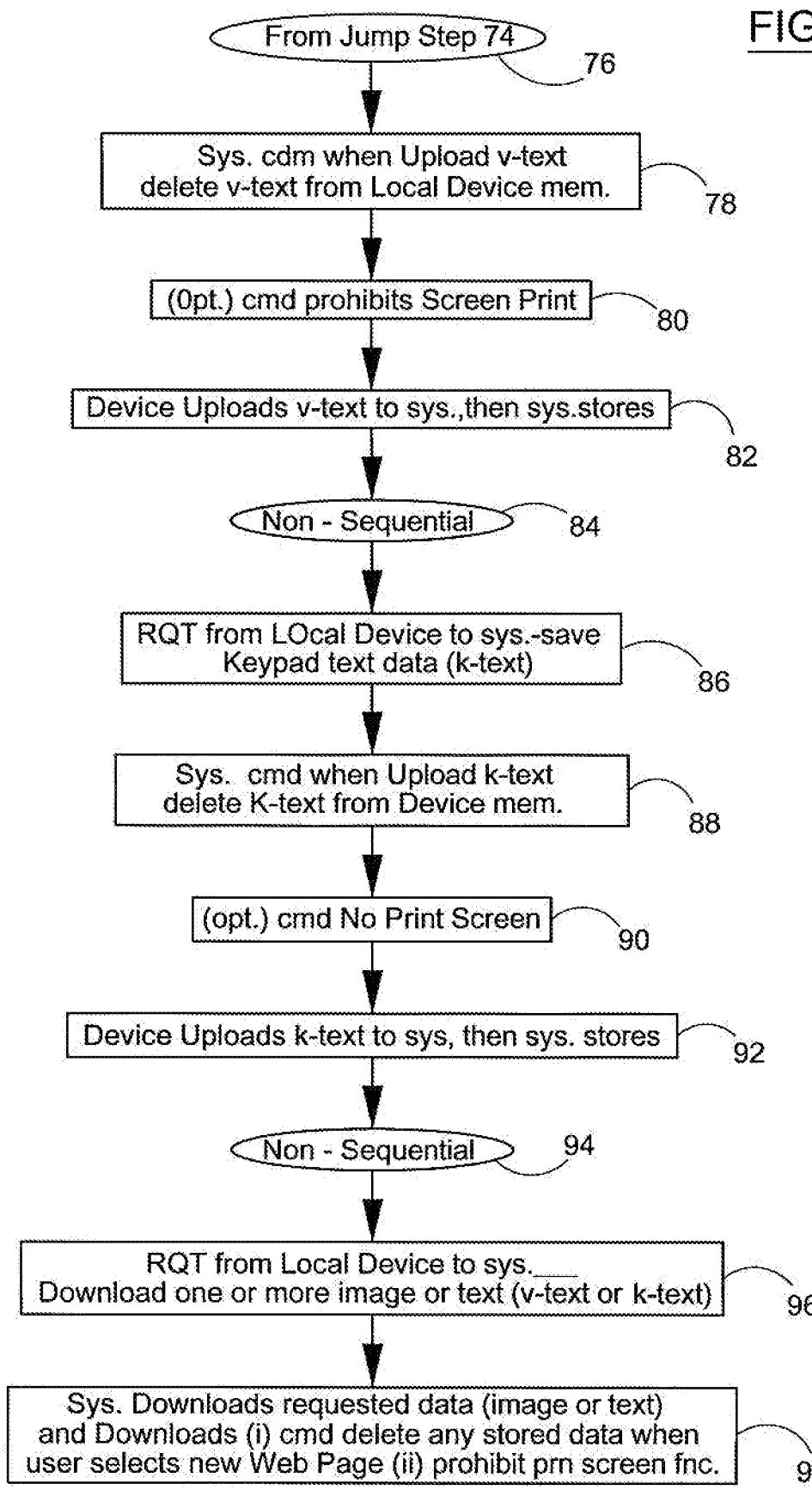

The present invention relates to a highly secure method for the acquisition, processing and production of healthcare data and service records implemented in a cloud computer network. In order to provide a seamless system which can accommodate a number of different devices such as desktop computers, Apple™ mobile devices (using IOS operating systems) and Android™ mobile devices (using an Android OS or operating system). The cloud based system is agnostic to the computer device coupled to the system via a telecommunications network. Additionally, with the use of Microsoft™ SQL database in the cloud-based healthcare data-service system, other computer database systems can be mapped to the inventive cloud-based healthcare data-service system by mapping the fields of the cloud-based healthcare data-service system database to the other computer system.

The cloud-based healthcare data-service system and method uses the power of the .net programming platform to create a secure cloud based web application that seamlessly interacts with mobile devices that utilize the IOS and Android™ platforms. The system's mobile platform also integrates the Google Glass™ and mobile camera systems and other wearable technologies such as a smart watch. The system and method also has five unique apps on the mobile side that work with the different types of users. These apps include (a) the provider/physician app, (b) the patient app, (c) the staff app and (d) the referring doctor app. A mobile camera systems app can also be integrated into the cloud-based healthcare data-service system and method by using the modules and inventive techniques described herein.

The cloud-based hardware setup is very simple and relatively inexpensive. It includes apple TVs™, regular TV monitors, thin clients, and smart phone devices. These devices are setup with a reliable Internet connection and good secure wifi connectivity. The system and method provides options for the user to install the program on a local server if desired for local back up, however, all data is backed up and secured and protected and encrypted in a secure cloud-based database server and networks.

No PHI (personal health information) is stored in any of the native or local devices. The system and method also enables the user to have rich interactive consultation and communication with the patient by leveraging the apple TV™ airplay/mirroring technology.

The system and method model is a total healthcare solutions package to include, as an example, the modules in the following Table.

TABLE

| Examples of IT Modules |
| --- |
| A total EMR system |
| A total practice management system |
| Image management system |
| Document management system |
| Insurance eligibility verification system |
| Billing system |
| HIPPA compliance and management services |
| Network, hosting and general IT support services |
| Marketing and SEO and social media management services |
| Hardware dashboard setup and maintenance services |

The system and method platform aims to integrate and simplify all such services under one roof. This is a unique proposition that has not been done before.

Section: Cloud Application (Web Version).

Figure 14A:
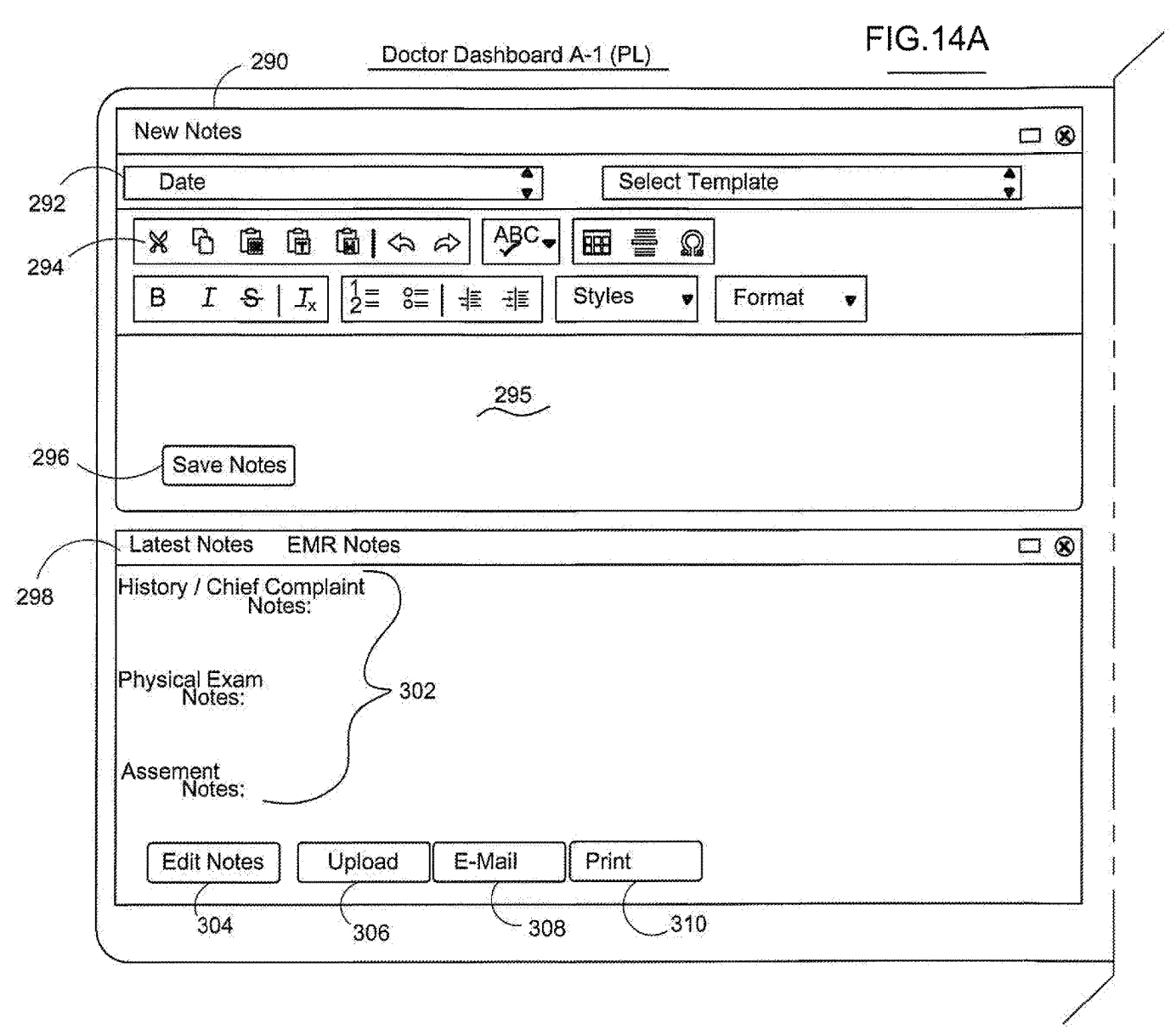

The system and method has 3 dashboards, a Main Dashboard, FIG. 6, which permits the owner or chief administrator to control major aspects of the system, a Patient Layer Dashboard, FIG. 13, which deals with items and data in a patient-centric manner and a Doctor Dashboard, FIGS. 14A and 14B, which primarily functions to present healthcare professional data at the physician level.

Section: System Overview—FIG. 1

FIG. 1 diagrammatically illustrates system diagram 10 which shows a cloud based system 12. In the cloud or internet, a processor 14 operates with one or more programs 18 and coordinates with a database DB 16. In the present embodiment, database 16 is a Microsoft SQL™. The computer based system has a plurality of input/output devices 20 which permits various healthcare workers and also the patient under treatment to access information in database 16.

Therefore, the system includes a treating physician or doctor 24 who utilizes a smart phone (Smph, a tablet Tblt or a desk top computer PC, generally designated as device 22 in FIG. 1). The treating physician device 22 communicates via a telecommunications network 13 through an input/out device 20 to the cloud based system 12. Data is stored for the healthcare provider HCP in database 16 and is processed by processor 14 executing program 18.

Patient 28 also has access to the unique patient records via smartphone Sm-Ph or tablet Tblt or desktop PC (device 22). Patient 28 can have access to his or her records on database 16 at least on a limited manner.

Most treating physicians utilize healthcare HC staff 26. Healthcare staff 26 also use one or more devices 22 which access the patient records in database 16.

Related or referral healthcare providers HCP 30 also access and upload healthcare data into database 16 via devices 22. In addition to processing patient data in the cloud based system 12, the system is also designed to interact with lab diagnostic computers 34 via the appropriate input/output device 20. Since the patient data is located in the Microsoft SQL™ database 16, the lab diagnostic data sent as an electronic form can be mapped into the cloud based system 12. In a similar manner, vendors of healthcare HC goods 32 as well as e-prescription or electronic prescription providers and other online health kit providers may be electronically linked in some manner to cloud based system 12. Financial and accounting 38 management computer system can also access the cloud based system 12. Further, the treating physician and his or her staff can issue a billing request and insurance reimbursement request to billing and insurance computer system 36.

Section: Agnostic Acquisition and Processing System—FIG. 2

FIG. 2 diagrammatically illustrates the agnostic acquisition and processing system in accordance with the principles of the present invention. Database 16 is linked to telecommunications network 13. The system is agnostic because data 41 from Apple™ device operating in IOS operating system 40 communicates image data, audio data, voice to text data as well as text data via telecom network 13 into database 16. The term "voice to text" refers to audio files which are captured by the mobile device or the desktop and which are converted into text by speech recognition modules. The term "text" in connection with FIG. 2 refers to keypad input text data input by the user into the keypad of the device.

FIG. 2 also shows that it is compatible with Android operating system 42 and permits that Android operating system and, more accurately the device executing the Android OS to upload and download image, voice to text and text data. A desktop OS 44 is on a non secured site. This image data voice to text and text data is also potentially uploadable into telecom network 13 and database 16. A non secure site would be generally equivalent lab diagnostic 44 or vendors of HC goods 32 in FIG. 1. New secure computer devices have severely restricted access to database system 12.

FIG. 2 also shows a desktop operating system at a secure site 46. The term "secure site" refers to a site that has established a high level secure communications pathway (e.g., SSL) with the cloud network and database 16. A desktop OS secure site 46 permits local storage of the image data, voice to text data and keypad text data to the local storage in accordance with security protocol established by the cloud based system 12. As discussed later, users are assigned "permission" which permits the user to process certain data (or not) and download and upload certain data.

With respect to IOS devices 40, android OS devices 42 and desktops, FIG. 2 shows that in generic step 48, the cloud system 12 blocks local device storage and blocks a print screen function (fnc). After executing function block 48, the system executes a generic processing 50. As discussed later, any and all steps in the present invention may be sequentially reorganized to operate more efficiently. Unless otherwise stated, the sequence of execution of any particular function is not important.

Section: Generic Agnostic Acquisition and Processing Flow Chart—FIG. 3A and B

FIGS. 3A and 3B describe generally an agnostic acquisition and processing flow chart in accordance with the principles of the present invention.

General agnostic flowchart 52 begins as functional 54 wherein a request to (rqt) is made to save an image recently acquired from a local device 40, 42, 44, 46 and to save the image by uploading the same to the system 12. Step 56 recognizes that earlier, when the App or application was initially downloaded into the local computing device, the App has a command (cmd) which permits the local device to upload the image and substantially immediately thereafter delete the image data from a local device memory (mem). The delete image cmd is downloaded with the page display that provides the user a selectable "save" command cmd. The command may have been downloaded by the cloud-based healthcare data-service system 12 when the App was loaded into the mobile device. The pre-loaded code is activated when the mobile device requests an "upload image to the server" sent to the system 12.

Examples of current software routines which accomplish this delete image data from local memory are listed below.

During an upload from a mobile device that has acquired data (for example, an image taken by the mobile device camera), the app on the mobile device sends the image data along to the cloud-based healthcare data-service system with the other necessary parameters (HCP name, User name, Patient Name, type of Image).

The following is the current method in iOS to delete the captured image from the local device memory using the app on the local device (subject to the "upload image request" from the mobile device to the cloud-based system):

(BOOL)removeItemAtPath:(NSString*)path error:(NSError**)error NS_AVAILABLE(10_5,2_0).

File file=new File(getStorageDirectory(activity),directoryName);

FileUtils.cleanDirectory(file).

For Android™ operating system. the following is the current method to delete the captured image from the local device memory:

File file=new File(getStorageDirectory(activity),directoryName);

FileUtils.cleanDirectory(file);

Although the present system uses MS SQL™ on the central computer 12, an Apple IOS™ on one local device 40, an Android™ on another local device 42, the principles of the present invention can be applied to desktop OS (such as Windows™), Oracle™ databases, Linux™ OS, etc.

In step 58 (FIG. 3A), a command (cmd) is optionally provided from the central server and operating system to the local device to prohibit a screen print (prn). The cmd may be pre-loaded into the mobile device when the App was initially downloaded from the system 12. Step 58 is optional in that in some instances a local device should be permitted to print screen. For example, if the local device was a healthcare provider HCP related or referral medical officer physician 30 (FIG. 1), then a print screen would be appropriate while the referral physician 30 is active in the cloud based system. A "permissions" list is associated with each user profile (a UPP or User Personal Profile) which dictates permissions that the User has in connection with the operation of the cloud-based healthcare data-service system.

In step 60, the local device uploads the image to the central server and the database 16. The processor 14 executing program 18 saves that recently captured image to database 16. Step 62 recognizes that the subsequent steps are non sequential events or actions executed by the cloud computer system and the local device.

In step 64, request from a local device is made to the cloud system 12 to save an audio record. In step 66, the command which permits the uploading of a audio record then commands a deletion of the audio record from the devices local memory. The delete audio record (or text representative of audio record) command is embedded in the then displayed page shown to the user. Step 68 recognizes that the local device uploads the audio record into the system which is then stored in database 16 associated with the particular patient record.

Step 70 recognizes that the following steps are non sequential. Step 72 recognizes a request from a local device directed to the system to save text data created by a speech to text generator. In other words, the treating physician 24 may dictate into his or her mobile device physician's notes. The mobile device may have a speech recognition module therein which translates the audio record into text. In this sense, the mobile device has a speech to text generator. Step 74 jumps the program from FIG. 3A to FIG. 3B. Step 76 recognizes this earlier jump step.

In step 78, the App commands the local device to upload the voice to text and then delete both the audio record and the text generated record from the memory of the local device. Step 80, which is optional, downloads a command from the cloud based system 12 which prohibits the local device from printing the screen with the text record. This "no print" may be a cmd downloaded with the App. Step 82 recognizes that the local device uploads the voice created text to the cloud based system 12. Cloud based system 12 then stores the text in the appropriate patient record in database 16.

Step 84 recognizes that the following steps are non-sequential with the previous steps. Step 86 is a request from a local device to the system to save keypad input text data into the cloud based patient record system. Step 88 recognizes that the App command, which permits the upload of keypad generated text into the cloud based system 12, deletes the keypad generated text from the memory of the local device 40, 42, 44, 46. Step 90, which is optional, recognizes that cloud based system 12 downloads a command prohibiting the local device to print the screen bearing the keypad issued text. Step 92 recognizes that the local device has uploaded the keypad text to system 12 and then system 12 stores that keypad generated text into the appropriate patient designated record.

Step 94 recognizes that the following steps are non-sequential with the preceding steps. Step 96 is a request from local device to the system to download one or more images or text data from cloud based system 12 into the particular local device 22 (FIG. 1). Step 98 recognizes that the system downloads the requested data (whether that data is image data or text data) and downloads (i) a command to delete any stored data when the user selects a new web page and (ii) prohibits the print screen function on the local device.

With respect to the Surgical Scheduler Flow Charts in FIGS. 4 and 5, those figures are discussed later in connection with the Mobile System and the Health Care Professional Scheduler, FIG. 31. However, the Surgical Scheduler in FIGS. 4 and 5 can be implemented at different points in the system, such as in the Doctor's Dashboard (FIG. 14A, B) and the Patient Layer, FIG. 13 (see the "Schedule" function in FIG. 13).

One further example of the Administrative dashboard includes the following modules or functions:

TABLE

Example Admin Dashboard Table (Desk Top)

User Management
Cosmetic Quote (generic HCP bundled service quote)
Inventory Management
Reports
Settings

TABLE

Example Admin Dashboard - User Management

Manage Company
Manage Location
Rules and Permissions for Groups/Facilitating
Manage Users The Admin Dashboard houses all the controls, such as the user controls, to include administrative management of the cosmetic quote module, the inventory module, a reports sections (which generates financial and marketing and scheduling reports among others), and a general settings section for application setup for emails and merchant services.

The administrator can monitor and give access and track the usage of the application. This is accessed through a menu selection. Upon clicking the appropriately identified button function on the display screen, the Admin dashboard will be presented and then allow the user/administrator to use this Admin Dashboard.

Section: Main Dashboard General Controls—FIG. 6

The main sign-in dash board houses all the general controls of the application. This area allows the user to enter HC patient information (also can be viewed on our mobile app as shown, schedule appointments, create and customize templates, inventory area to organize the office inventory that is separated into categories, the ebilling section that communicates with NueMD™ interface, letter generation area to create and customize letter, organize faxes, utilize the message board to send and receive messages and important faxes and emails from the users, staff and patients.

FIG. 6 diagrammatically illustrates the main dashboard which the user sees if the user has access the secure cloud based system via a desktop. The initial main dashboard screen permits the user to conduct a patient search 134 or to add a new patient 136. Also, the main dashboard identifies the current user 138. If the user has the appropriate permissions (previously logged in to the user personal profile UPP), a drop down menu permits the user to access the administration control. This dropdown menu is shown as block 140 in FIG. 6. From the main dashboard, the user may select template builder 142, pathology reports 144, letter generator 146, message center 148, or an upload files module 150. Also, the user can access patient information 152, scheduling module 154, file sort module 156, and inventory 158.

Section: Administration (User Management)—FIG. 7

FIG. 7 diagrammatically illustrates the administration dashboard which a user can select if he or she had the appropriate permissions as set in the UPP. The administration dashboard has activated user management function 160. For that user management module 160, the user can select companies 162, offices 164, locations 166, user based offices 168, users module 170, and role and permissions module 172.

The user can also select different major modules such as cosmetic module 174, inventory management module 176, reports module 178, scheduling parts module 180, e-fax message module 182, and settings module 184.

The following is an example of the interactivity of Admin Dashboard for practice management.

| Table Example: Practice Management (Admin) Dashboard (Desktop) |
|---|
| Patient Info |
| Scheduler |
| Inventory |
| Template Builder |
| E-Billing |
| Message Center |
| E-Fax Messages |
| Help |
| Pathology Reports |
| Letters |
| Appointment List Report |
| All Transaction List Report |

Section: Administration Layer Menu Tree—FIG. 8

FIG. 8 diagrammatically illustrates the administration layer menu tree. If user selects user management 160 module, the user can optionally access company files, offices, locations, user based offices, user and role permissions modules 162-172. For cosmetic quote module 174, the user can select manage procedures, manage miscellaneous activities, and manage facilities and times grouped as functional modules 186 in FIG. 8. If the user selects inventory management 176 module, sub-modules involving product details, vendor details, and purchase product details are available. Reports module 178 leads to appointment list report which is described in another figure and an all transaction list report which modules are generally identified in FIG. 8 as function blocks 190. The scheduler parts 180 module leads to problem and sub problem module and appointment and purposes modules, grouped as functional block 192. The e-fax message module 182 is described later. The settings module 184 as sub module for email configuration and Paypal or payment configuration as functional group 194.

Further examples of functional modules for the Main Dashboard which permit the user to access other documents are shown below.

| TABLE |
|---|
| Example Main Sign-In |
| Patient Info |
| Scheduler |
| Inventory |
| Template Builder |
| E-Billing |
| Message Center |
| E-Fax |
| E-Fax Messages |
| Help |
| Pathology Reports |

| TABLE-continued |
|---|
| Example Main Sign-In |
| Letters |
| Appointment List Report |
| All transaction List Report |

This Dashboard has many unique features in it.

| TABLE |
|---|
| Example User Personal Profile (UPP) |
| Name |
| Email ID |
| Date of Birth |
| Gender |
| Marital status |
| Cell Phone Number |
| Home Phone Number |
| Work Phone Number |
| Address 1 |
| Address 2 |

Section: Inventory Screen

The Inventory functional module permits the Admin User to control inventory in the HCP facility. The inventory may be items consumed by the HCP while delivering the HC service to the patient or may be items that the patient may purchase from the HCP. The system and method establishes a user friendly platform to replenish supplies and/or to sell items to patients.

Section: Inventory (Administration)—FIGS. 9A and 9B

FIG. 9A shows an inventory screen which in row 196 identifies the product name, the quantity in stock, the current quantity selected by the user to be sold or delivered to the patient, the base price or rate for that unit, a discount amount, and the total amount due. In function 198, the user can remove the previously entered quantity. In row 202, a total amount is provided, both for the discount and the amount for the goods to be delivered to the patient. In row 204, a global discount is provided. For example, if the patient is undergoing several types of treatments, and needs follow on care, involving several different types of creams or lotions or bandages, that patient may be given a global discount for that combined service. In row 206, the total amount is shown and the total discount amount is shown as well as the total amount after discount. The user has access to functions sell 208, internal use 210, cancel 212 and add more products 214. The "internal use" function indicates that the patient is not independently charged for that item.

FIG. 9B shows another inventory administration screen. In this screen, the user can search a product by inputting the product name into search block function 216. Row 218 shows the SKU barcode for a particular product, the product type or category, the product name, the total amount or quantity in stock on hand for that facility, office or business, and permits the user to add a quantity by activating function 220.

Further examples of the inventory module may include the items in the following tables.

| TABLE |
|---|
| Example Inventory Screen Table Display |
| Search Product |
| Bar Code |
| Product Type |

TABLE-continued

Example Inventory Screen Table Display

Product Name
To Stock Quantity
Add to Cart

This inventory module is where the HCP operating the cloud-based healthcare data-service system has a list of products that are sold through this software. The module serves as a point of sale area where the user can simply click and add an item or items to a shopping cart. Once done, the screen prompts the user to the following screen, which will enable the user to conduct the transaction. Alternatively, the software generates a unique bar code for each product category as shown below.

TABLE

Example HCP Selects Product(s) to be Sold to Patient

Product Name
For Location
Vendor Name
Barcode
Expiry Date
Cost Price
Selling Cost
Disc On Price
Product Details
No. of Qty.
Note
Inventory Current Status
Min Stock Range
Stock in Inventory As for the mobile implementation of the inventory module, an IOS device can easily scan and read the bar code from the product and can then generate the point of sale similarly. Not only does the smart phone read and scan the bar code and do the point of sale transaction, it also records the product in the patient chart and sends a report to the patient through the patient app. The screen shot below is an example of the cloud web-based version.

TABLE

Example HCP Authorizes Sale to Patient

For Patient
Product Name
In Stock
quantity
Rate($)
Disc.($)
Amount($)
Remove Items
Total Amount
Global Discount
Total Amount: $165.00
Total Discount Amount $0.25
Total Amount After Discount: $164.75

Once the transaction is complete, an invoice is generated and the user is allowed to choose to send, print, fax, or email the quote or invoice. Alternatively, the user can also take payment through the payment button, which will direct the user to PayPal™. At that payment processor, the user can select the necessary patient code to charge the patient for the goods sold. Alternatively, other instant payment processing modules can be used. In this area, the appropriate transaction can be completed. One unique feature of this design is that the entire module works seamlessly with the IOS device. The inventory section of the provider/physician app and the staff app on the IOS device mirrors the same functionality and also utilizes the bar code reading capability inherent in the device to simply point and read the code and make the transaction happen.

TABLE

Example Product Sale Communication

Print Quote
Email
e-fax
accept payment on current screen

TABLE

Example Payment Profile

Order Summary
Credit card data
Billing data

Section: Calendar Schedule (Administration)—FIG. 10

The cloud-based healthcare data-service system and method has a calendar module for (i) scheduling appointments and (ii) surgery and (iii) pre-op events.

FIG. 10 diagrammatically illustrates a scheduling program for a number of physicians via the cloud based system 12. In columns 224a and 224b, and 224c, different physicians daily schedules are noted. For the physician in column 224b, that physician has a schedule appointment 226 between 10:30 and 11:00 am. In area 228, the user can input or select a particular physician from a group of physicians. This may be accomplished by a pull down menu screen listing all physicians at that facility. Otherwise, in area 230, the user can select an appointment type. One type of appointment may be a surgical operation whereas another type of appointment may be a consultation event.

Section: Template Builder.

The Template Builder functional module of the cloud-based healthcare data-service system permits the user to generate custom templates or workflow charts or requirements for a particular health related event. With the Template Builder module, the physician can have a preformatted form to take care of common situations encountered in the practice. The Template Builder software module uses step by step task assignment software. Other HC professionals, such as a staff member, can create custom templates for the common functions performed by them or others in the HCP facility, which do not require the immediate input or consultation with the physician.

The administrative staff uses the template builder (TB) to create forms and form letters that are common to send to insurance companies, to other referring or primary care or related care physicians, and also to places of employment and to schools. This TB module is accessible from a variety of other dashboards and user interactive screens in other sections of the application utilized by various different personnel in the HCP office setting.

Access is also provided form the TB template module to an interactive screen sometimes referred to herein as a "meaningful use" interactive module. An example of a meaningful use module is the Vitals module discussed in connection with FIGS. 25 and 26. The meaningful use module(s) are oftentimes mandated by the U.S. Government and other governmental agencies to document certain key HC data points. Providing access to the TB template module in connection with the meaningful use functions enables an HCP office to modify, change and follow the ever-changing requirements mandated by the government and/or the insurance companies.

The template builder module also has special controls that enable the user to directly import any images taken by the IOS devices and/or Android™ devices including Google Glass™ or the mobile camera systems into the EMR HCP notes. Seamlessly integrating images and uploading the same into the cloud-based healthcare data-service system 12, in real time and substantially instantaneously is a new feature of the comprehensive, highly secure system and method. See FIGS. 3A and 3B.

An example of this function involves a user taking an image of a setting on a laser that is used and is, then, make that image a part of the doctor's encounter note in the EMR. This information of the laser settings normally is transferred onto a sheet of paper by the HC staff from the computer screen and then is manually entered by the HC staff into the encounter note. Now, by simply taking a photo of the screen, the image is imported automatically into the database of the cloud-based healthcare data-service system, allowing the image to be seen in the settings in the EMR note as an image. This image capture by a mobile device, carried and operated by the HCP staff, shortens the time and steps necessary and makes the process of efficient health care delivery more efficient. See FIGS. 3A and 3B.

Another unique design feature of the TB template module is to have yet another control that enables the user to directly transfer voice to text into the preformatted template. The usual workflow of a physician is to confirm the preliminary history taken by the staff and to review it with the patient. Such information can be part of a preformatted template. The physician then performs the physical exam and documents the findings and the plan of action. This TB control allows the physician to simply use the IOS smart phone device to dictate into the device and the voice to text converted material populates the note at the appropriate area of the note. See FIGS. 3A and 3B.

The overall concept idea is to integrate the IOS smart phone device and the cloud-based web system and method to work seamlessly together in real time.

Further examples of template builder functions follow.

TABLE

| Template Builder Example I |
| --- |
| Add Image to Process Template |
| IVR Input each process step |

TABLE

| Template Builder Example II |
| --- |
| New (establishes a "new" template) |
| Save |
| Cancel |
| Preview |
| Day of the week / date |
| Food limitations (Cold Drink - Hot Coffee) |
| Location - Patient Activity (Tourist-Place, Thailand) |
| Type Note on word processor |

Section: E-Billing

The e-billing functional module uses a grid with the necessary patient information and the insurance details. The grid presentation for the insurance billing module is presented each day to the HCP staff The entire schedule for the HC provider is populated in this grid as shown below. This functional module permits the user to enter the necessary CPT and ICD insurance codes along with the modifiers for the day for all of the patients in this one modular interactive screen area and to upload all this information to the cloud-based healthcare data-service system. At the cloud-based healthcare data-service system, an interface is used to transmit the billing data to the NueMD™ bill processing system. This bill processing system processes these HCP insurance claims. Exemplary tables follow with the functional aspects of the e-billing.

TABLE

| Example: Patent Data and Insurance Processing Table |
| --- |
| Patient Name |
| Date of Birth |
| Appointment Date |
| Insurance Name |
| CPT Code |
| Upload Date |
| Status |
| Upload |

The cloud-based healthcare data-service system also provides a communications pathway for the user to see the patient by allowing them to click on the patient name which will prompt them to see a photo of the patient and the necessary demographic information. The cloud-based healthcare data-service system 12 downloads the patient photo when the local device (desktop or otherwise) requests the same.

Alternatively, the user is able to upload any necessary supporting documentation in this e-billing section. Frequently, the insurance companies require physicians to send supporting documentation. Many claims are denied due to the same reason. Therefore, this e-billing interactive screen grid and section now allows the physicians or the HCP staff to upload and electronically send any such supporting documentation.

Another aspect of the cloud-based healthcare data-service system is that the insurance coding capability works in real time through the IOS application. The user can assign the CPT, ICD insurance code to the HC event, and also modifier codes on the mobile side of the system and method application. The App then seamlessly communicates with the system 12 and populates that information in this e-billing grid with the appropriate patient data. This allows the user to capture more codes instantaneously.

Section: Message Center

The message center permits the user to send faxes or process incoming faxes, have those faxed EMR documents reviewed, as important messages for the day for the HC staff or physician, send and receive emails, and serves as the place to check all important messages. The fax module has a feature that allows the user to tag a fax as an important fax that has to be reviewed by a physician and then sends that fax to this message center to be reviewed.

Also any important labs or other documentation that has to be reviewed by the physician is distributed by the HC staff member to the doctor. This minimizes any omissions or errors regarding review of such important information.

A message board is presented to each user when he or she opens many of the interactive screens which are part of the App, downloaded as interactive screens and operated in conjunction with the cloud-based healthcare data-service system. In the IOS device, the user is able to review all types of messages that at his/her convenience.

Section: E-Fax Message Center (Admin)—FIG. 12

Figure 11:
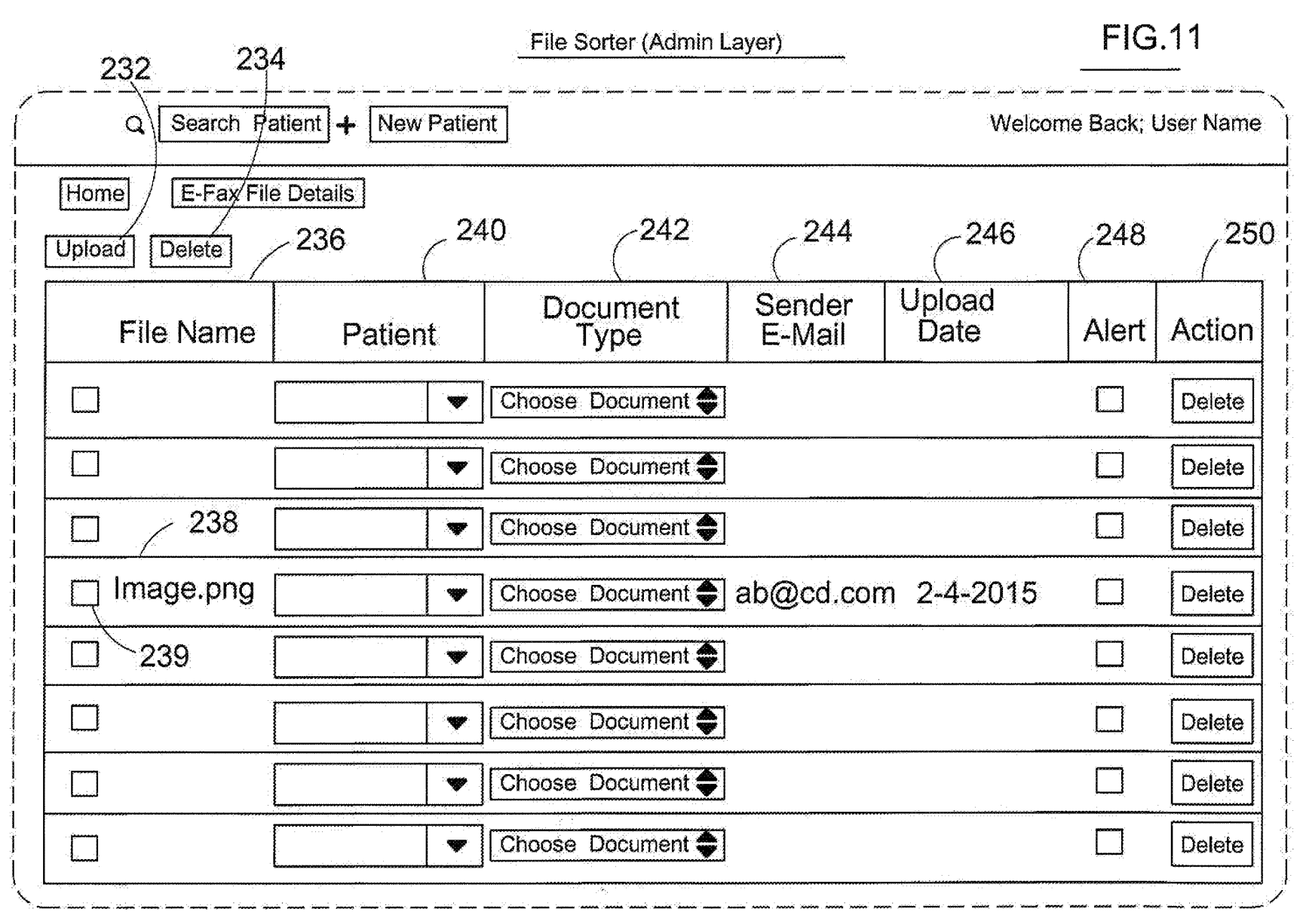
Figure 12:
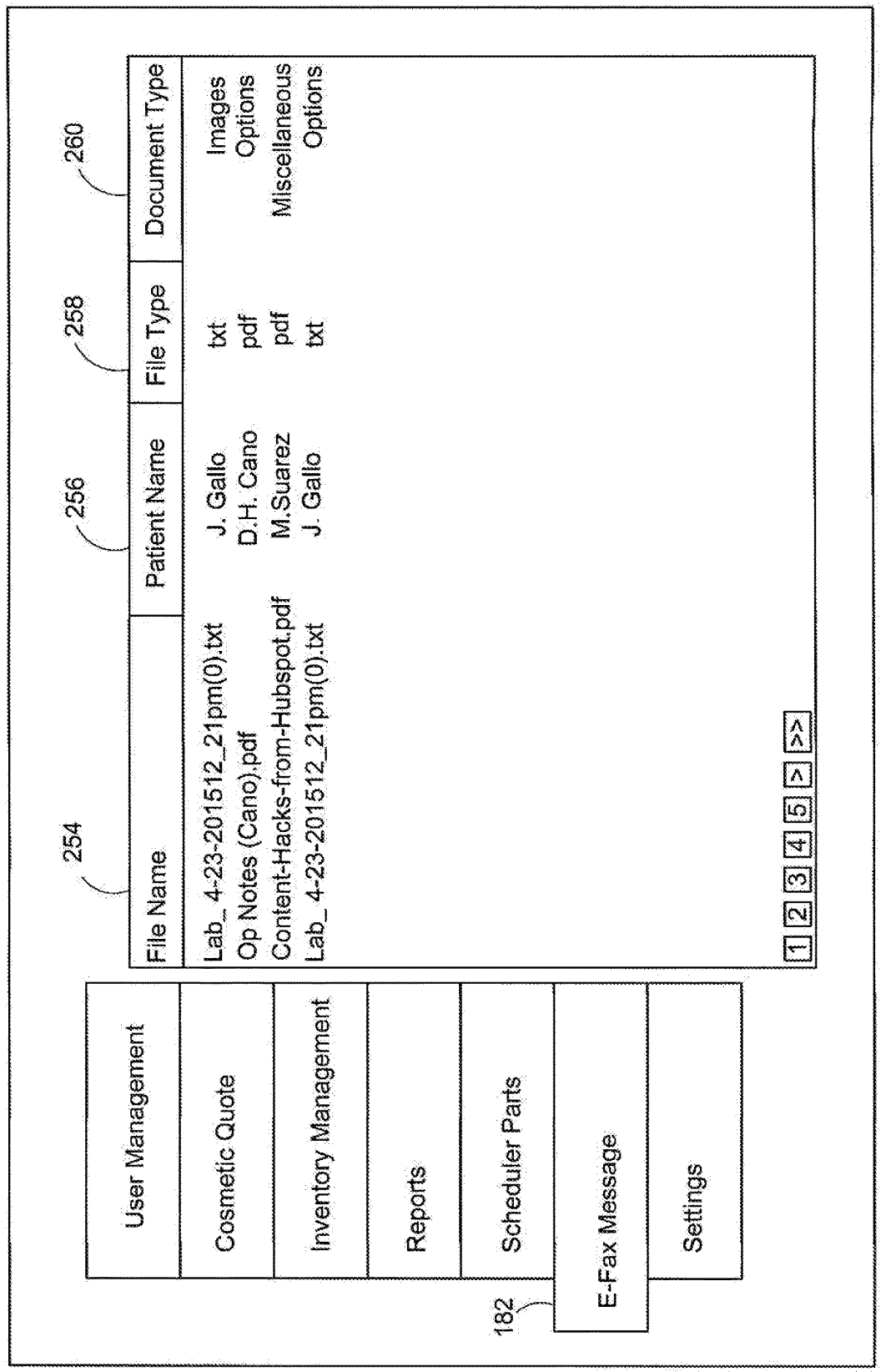
FIG. 12 diagrammatically illustrates an E-Fax Message Center (Admin Layer) screen (discussed before FIG. 11).

FIG. 12 diagrammatically illustrates the electronic or e-fax message center user dashboard. The e-fax message module 182 has been selected by the user from the Admin User Management interactive screen in FIG. 7. Column 254 shows the file name. Column 256 shows the patient name, column 258 shows the file type 260 shows the document type. These items have been selected by the staff or the doctor from FIG. 11. Otherwise, these are electronically faxed in documents or email messages unique to a particular patient.

Further examples of the message center functional aspects are discussed below.

TABLE

Example: Message Center Table

Search Patient name
Inbox (lists all incoming messages)
Sent (function or "fnc")
Compose fnc
Add Document to Message fnc
From
Subject
Date Section: Document Management File Sorter (Admin Layer)—FIG. 11

The Document Management Module is sometimes called a File Sorter Module and is an interactive screen that permits the user to quickly tag, identify, and forward, if necessary, documents electronically presented to the HC facility.

FIG. 11 diagrammatically illustrates a file sorter functional module for the present invention. As noted, the user can search for a particular patient or add a patient to this file sorter. The user can select a file by activating functional block 239. In this situation, the document labeled "image .png" in block 238 would be uploaded once the user selects upload function 232. Alternatively, the user could delete image file 238 by selecting function delete 324. A double check question "do you want to delete" may be presented to the user before the file is deleted. The patient's name is shown in block 240, the document type is shown in block 242, the sender's email is shown in block 244, the upload date is provided at block 246 and alert is activated in column 248 and the action is shown in column 250. The alert is used to notify the physician that this document should be reviewed. See, for example, the Doctor Dashboard described later.

The patient's name in region 248 may be located, for a unique inbound document, by a pull down list showing all the patients in an alphabetical order. Otherwise, the cloud-based healthcare data-service system could attempt to match the patient's name with the "patient name on the inbound document." In other words, once the image has been uploaded into the system, for example from a referring physician 30 (FIG. 1), the patient's name in the HCP's system must be associated with that image 238. The user can select the patient name by selecting the patient from an alphabetical pull down list.

The type of document has to be identified as being associated with that patient. The system may permit the user to click on "image. png 238" to show the use what type of image it is (a lab report as compared with an image of an injured hand). If it is a lab image or an image of an injured body part, that type of classification may be selected by the user from a drop menu at column 242. The sender's email in column 244 may provide a clue to the user as to what type of document it is. Lab work can easily be identified because those labs are typically independent of other facilities.

The File Sorter or Document Manager is presented as an interactive grid that is populated by all the incoming efaxes that are to be configured by the application. The faxes for the day are provided in the grid. This grid also allows the user to select the patient from a drop down menu and also the pertinent folder to which the fax should be attached.

TABLE

Example: Document Management Table

E-Fax File Details
File Name
File Type
Patient
Document Type
Is-Important
Images
Labs
Radiology
Pathology In this manner, all of the faxes for the day can be very easily directly attached to the respective patient data folder and the respective folder in one easy-to-use screen. This interactive screen also allows prioritization of a fax as important by checking an "alert" grid to the far right. This checking ALERT sends this important fax to the provider/physician's message board to be reviewed. All the faxes can be uploaded at once. This interactive screen also allows the user to see or view the fax and know what it is by clicking on the document thumbnail image as it appears on the interactive screen. This prompts the user for indicating what type of fax it is and to whom it belongs and in what folder to input the document.

In order to provide a back up mechanism such that no faxes are missed, the fax messages module stores all of the faxes for review in the future if necessary.

Section: Document Management—Pathology or Lab Reports

The cloud-based healthcare data-service system 12 has another functional module unique to certain, easily defined type of HC data, such as "pathology." The name pathology is only exemplary here, it can be changed to whatever the user requires. There are certain documents, such as pathology reports or mammography reports or EKGs, for example, that should be reviewed, confirmed and signed off by the physician. The Document Management module is where the user can designate whatever documents that he/she deems crucial to review and sign off.

The Document Management module can also be used to create a workflow or Process Template that works with HC staff or the physician. It is oftentimes cumbersome for physician to look through all the faxes of the day or for the staff look through the faxes and tag and print the documents and/or send separate emails regarding these documents. With the cloud-based healthcare data-service system, the physician has an interactive screen and structured module which will assist in (a) reviewing the docs and (b) rerouting the docs as required by best process practices.

TABLE

| Example: Pathology Report Table |
| --- |
| Search for Patient name |
| Select a template |
| Preview doc |

The File Sorter—Pathology or Lab Reports Module works to supply doctor-centric reports to the doctor. In the Doctor Dashboard, FIGS. 14A and B, the specific doctor assigned to the treat the patient will comment on the report as noted in connection with FIG. 15.

Section: Letter Module as a Template Builder

The letter functional module is an interactive screen area that works with the template builder for the user to generate custom letters to different parties seamlessly as shown below.

The user can select the "type" of letter template and then select the patient name and send this template letter directly to the patient through their app, or print it, or email it, or fax it to the selected destination. The objective of this module in the cloud-based healthcare data-service system is to completely eliminate or significantly reduce paper and use the patient app to send this HC information to the patient or to the referring doctor or facility.

This letter module section allows the HCP to send thank you letters and other documents to the referring doctor through the referring doctor app as well.

Section: Financial and Marketing and Scheduling Reports

The financial and marketing reports section is an interactive module wherein the user can generate various financial and marketing and scheduling reports, such as financial activity of the day or week or month or year, the appointment lists, appointment types categorized by problem, etc.

Customizable search criteria further serves the practice management side of a physician's office. Reports are generated that serve the necessary requirements for maintenance of certification for surgeons. The program can easily track the various types and number of procedures required by different surgical boards to maintain board certification. This can, then, be easily printed, emailed, or saved. In an alternative embodiment, the program works with the different surgical boards to directly upload this information to the boards' systems to further simplify the work life of the physician and the staff.

Section: Internal Chat—Messaging Center

The "Message Center" function is an interactive button, selectable on many of the system screens (see FIGS. 13, 17, 19, 20, 21, 23, 25) and permits the user currently viewing the screen to initiate and respond to inter-office or intra-office quick message chats without triggering the typical email function. In a sense, these message chats follow a "instant messaging"™ type system that was developed by AOL™. Many of the screens have access to an internal chat feature, which is located to the top right of the screen and is indicated by an arrow. This is the place where intra-office or intra-user instantaneous chat communication can happen to create an efficient way to communicate.

FIGS. 13, 17, 19, 20, 21, 23 and 25 show the message center functional button which calls up the message center for that particular user. When activated, the cloud-based healthcare data-service system 12 downloads the interactive message center screen to the user for further interaction by the use rand the system 12. All interactions run through the system 12.

Section: Patient Dashboard Layer (PL)—FIG. 13

The system and method can be generally broken down into a patient-centric layer and an admin-centric layer. A description of the patient layer follows.

The cloud based system 12 is conceptually separated into an administrative layer (described earlier) and a patient layer discussed hereinafter. The drawings sometimes refer to patient layer screen as "PL" and the administrative layer as "Admin." The patient layer permits the treating physician and the HC staff for that physician to process healthcare data, acquire healthcare data from the patient, process that data and provide adequate treatment for the patient's ailments.

FIG. 13 permits the user to search for a particular patient or to add new patient as well as identify the current user. In order to access the healthcare data and/or to access any aspect of the cloud-based healthcare data-service system, the user must input security words and passwords. The system and method then confirms the identity of the inquiring party, and if the security codes (or biometrics) clear, then the system and method permits access to the relevant interactive home screen.

In area 262, the current patient name is displayed. The user can select schedule appointment module 266, open personal patient information module 268, or activate appointment list module 270. The user can also activate doctor section 272, staff section 274, manage documents module 276, manage images module 278, obtain cosmetic quote module 280, activate pre-op or pre-operational pathway module 282 and open vitals (meaningful use) module 284.

An example of the patient dashboard interactive functions is shown below.

TABLE

| Example: Patient Admin Dashboard (Desktop) |
| --- |
| Panel A |
| Patient Information |
| Personal Information |
| New Patient |
| Schedule Appointment |
| Appointment History |
| Insurance Details |
| Eligibility Check |
| Panel B |
| EMR (Electronic Medical Records) |
| Staff View |
| Meaningful Use |
| Doctor View |
| Pre-op Pathways |
| Images |
| Doc. Management |
| Cosmetic Quote |

All areas of the system and method program application have a smart "search" button where the user can quickly search for any patient name, and the relevant patient data. This functionality is carried out throughout the cloud-based application, as discussed below. A grid appears below with an image of the patient and the necessary demographic information is displayed. Important and sensitive information such as the social security number is encrypted.

This patient dashboard is the place where most of the work, documentation, and other functions that are required to take care of a patient are located. All of these interactive screens allow the user to see an image of the patient to "jog" the HC staff's memory regarding patient encounters. There is a functional button located on the top that has the patient image. When the user's mouse is hovered over this button, a pop up of the image is visible for the user to be able to identify easily the patient and remember the patient encounter better.

This data is categorized into two sections. The patient information section has the patient personal information, schedule, appointment history, and insurance details and is used to check insurance eligibility. The second section is the EMR section. This is where most of the documentation and note creation occurs.

Section: Staff Section—Patient Centric Data

In the Patient-Centric Staff Dashboard, the HCP staff can conduct an eligibility check that enables the staff to "check off" all the necessary HC and patient information including, the copay, coinsurance, and other details that are important for the patient and the HCP office to know before rendering any services. This Staff Section works through an interface with NueMD™ software which is a third-party company specializing in e-billing and eligibility check-up services. This e-billing company can provide services through a seamless interface of the cloud-based healthcare data-service system program.

The other feature in the Staff Section is checking the appointment history of the patient in order to glance quickly at the types and number of encounters/appointments and also to review the proceedings of such encounters.

On the EMR side of the patient dashboard, there are unique designs, workflows and templates. The workflow template is configured with the mind that, taking care of a patient requires a team and not just the physician. Each member of the ancillary HC team has a different function and different documentation task.

In most situations, the patient is first encountered by the front desk. The front desk staff then checks-in the patient. A unique QR code is generated for checking in the patient. Once checked in, the medical assistant or the physician extender, such as the nurse practitioner or the physician's assistant, sees and documents several things, including the medical history, the meaningful use (e.g., vital) documentation, etc. Thus, these functions have been separated from the physician section of the EMR note to provide each user only the information that is necessary and to not clutter the screen with many pop-up screens.

Section: Staff Section—FIG. 17

Figure 17:
FIG. 17 diagrammatically illustrates a Staff Section (PL).

FIG. 17 diagrammatically shows a staff section interactive screen which enables the staff to call up various pre-programmed templates. For example, in region 356, the staff can select a particular problem that the patient is identified. In region 358, those problems could be a face with broken nose, a crooked nose, aging on the face or neck melanoma. In region 360, the staff user can activate a medication module, a return of service, a FHX, and a SOCHX. Region 362 enables the user to either identify a template that the user-staff member must complete for that particular patient. The user can save it or cancel the data collected.

Further examples of the staff view is listed below.

TABLE

Example: EMR Staff View Table
Test Patient (ID#7)

Age
DOB

TABLE-continued

Example: EMR Staff View Table
Test Patient (ID#7)

Gender
PMHX
PSHX
ALL
MEDS
ROS
FHX
SOC HX
Save
Cancel
Template

This EMR template on the Staff Dashboard is designed to serve different needs. Keeping in mind that some patients may not be an insurance patient and usually pay for services and may not require the extensive documentation mandated by the insurance companies, both options are provided to the HC staff via this dashboard interactive screen. For simple cases, the user can complete a simple form and enter the necessary information. If, however, a much more detailed form or template must be filled out, then a template button is provided and which allows the user to use a preformatted template or to create any number of new templates to satisfy needs of similarly situated patients or HC events.

The staff section design is also familiar to physicians. Colored tabs are provided to the left of the screen, which are reminiscent of the old patient charts that allow the physician and staff to quickly go to the areas of the chart that are for different problems.

The Staff Section interactive screen can also be configured as in the following example.

TABLE

Example Patient Management by HCP (Desktop) Table
Test Patient (ID# 7)

Age
DOB
Gender
Labs
Radiology
Pathology
Cosmetic Quote
Sold Product
Miscellaneous
Op Notes
Pre Op Instructions
Post Op Instructions
Medical Clearance
EMR Notes History The program easily organizes all the documents into easily viewable folders. The program is also able to send preoperative instructions and post operative videos and instructions directly to patients from the program to the patient's app.

Section: Meaningful Use—Vitals FIGS. 25 and 26

This is an area of the application where the government has mandated that certain data be entered and communicated and given to the patient.

Figure 25:

FIG. 25 diagrammatically illustrates a vital collection page for the staff. In row 460 the appointment date column is shown, appointment type, the problem associated with that appointment, a detailed or sub problem of that appointment, the status (complete or not complete) and capability to edit that record.

FIG. 26 diagrammatically shows a short list of vitals that the staff would complete by collected data from the patient. This is an example of a template. This includes, in the patient vitals block 462, entering data for the items on row 464 including height, weight, blood pressure and body mass index of the patient. Display region 466 shows a checklist such as medical reconciliation, tobacco use, tobacco cessation program, patient education, reminder, and a section for completion of the summary and referral to another HCP.

The following is another example of this interactive screen module.

TABLE

Example: Meaningful View Table

Height (in)
Weight (lb)
BP
BMI
Medication Reconciliation performed
Inquiry regarding Tobacco use done
Advised on smoking and tobacco cessation programs
Pt. specific education resources have been provided
Pt. was sent reminder via their preferred contact method
Summary complete and provided within 3 business days
Care transitioned from another provider
Save The template function can be activated from this View Screen. This allows the user to create more nuanced forms if the requirements for this staff section change in the future. A grid or a chart is shown for all the times meaningful use information is entered. This chart prompts the user to determine if all of the necessary information is entered by selecting "complete." Then the screen changes color for that displayed task. If not, the interactive screen prompts the user indicating that the task is "not complete" and further the interactive screen will not change color until the task is fulfilled by the user.

Section: Doctor Views—Doctor Dashboard

The doctor view or doctor dashboard is designed to present most relevant information to the doctor, given the current HC event, and further to be customizable on the fly, that is immediately customizable by the doctor for the then current situation.

Section: Doctor Dashboard FIGS. 14A, 14B

FIGS. 14A and 14B are generally placed on a desktop monitor such that the doctor, when using the current version of the present invention, can see a four quadrant screen. The four quadrant screen can be changed by the doctor as needed. However, in the presently illustrated embodiment, the quadrant left side (FIG. 14A) would include new notes section 290, EMR or electronic medical record notes section 298, and on the right patient images 312 and health history 326. Alternatively, the doctor may want to view as part of one quadrant, the vitals of a certain patient or the pre-operational or pre-op pathway for a particular patient.

With respect to FIG. 14A, new notes section 290 includes the current date 292 and permits the user to select a particular template 293 which should be completed by the user for that particular activity. The user is permitted to input into region 295 text relative the current notes. In region 294, there are various text functions such as copy and paste, undo and redo, spell check abc, make bold make italics, strike out, add subscripts and various indents or center. The user also has access to a calculator and a font style and format style. Function block 296 permits the user to save these notes input into text block region 295 into the cloud based system 12. In the lower left quadrant the EMR notes 298 are shown. The sub-divisions in region 302 show history/chief complaint notes; physical exam notes and assessment notes. The user has functional blocks edit notes function 304, upload function 306, email function 308 and print function 310. These functions are maybe activated for either the new notes section 290 or the latest notes 298.

FIG. 14B shows the right side quadrants of patient images 312 and health history 326. With respect to patient images 312, the user has enlarged one image of a hand of a user in image territory 314. In FIG. 14B, the patient image quadrant 312 shows a hand as image 314. The user can select supplemental images 316, 318 or scroll through a carousel of images 320. Further, the user can select forward button 324 or stop or pause button 325. The lower right quadrant shows health history 326. That health history may include a health code and text regarding the current patient. The user can select edit function or new problem module 328. Videos may be displayed and played therein with appropriate video controls.

Section: Doctor Dashboard Pathology Report—FIG. 15

Figure 15:
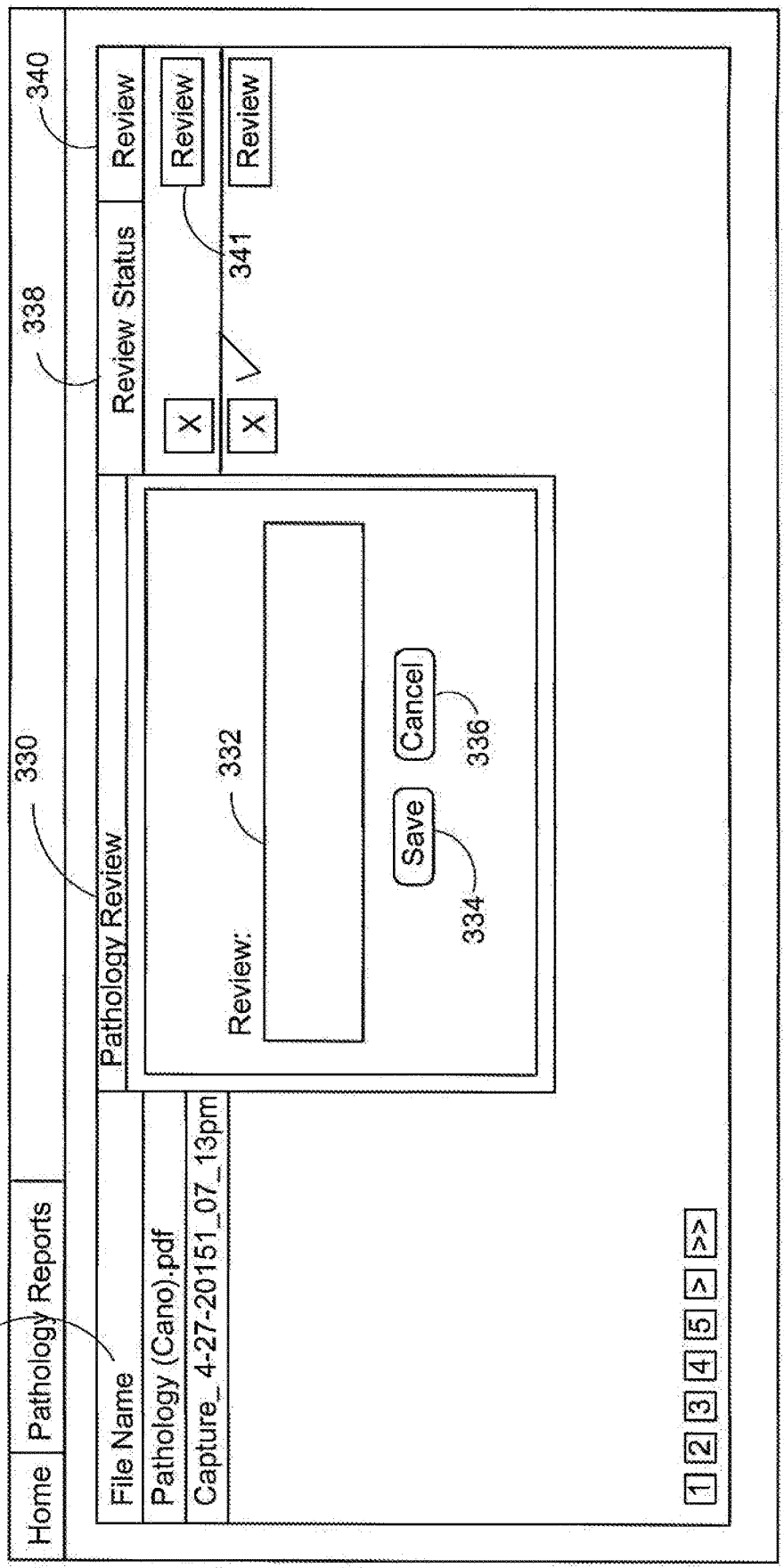
FIG. 15 diagrammatically illustrates a Doctor Dashboard C—Pathology Report (PL) (see Doctor Views, after FIGS. 17 and 25, 26).

FIG. 15 diagrammatically shows a pathology review block 330. In this block, the doctor has previously selected a particular electronic file for pathology, see review function 341 and pathology pdf under file name 339. After viewing the pathology report, the doctor would input text in review block 332. The doctor or HCP can execute save function 334 or cancel function 336. The user in review status column 338 can delete the file or can check off the file as being reviewed.

Section: Doctor Dashboard EMR Notes A—FIG. 16

Figure 16:
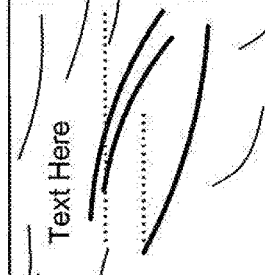
FIG. 16 diagrammatically illustrates a Doctor Dashboard EMR Notes A (PL)(see Doctor Views, after FIGS. 17 and 25, 26).

FIG. 16 shows doctor dashboard EMR notes A. The patient name and file number is shown in areas 342, 262. In display area 344, the user has selected the fourth appointment. Display area 346 shows the appointment date and time. A text block 348 shows the history and chief complaint, the physical exam and assessment. Image blocks 350 show various pictures of the hand of the patient which is subject to the complaint. Region 352 shows the second EMR note and region 354 shows the subsequent date of that EMR note. The user can select print function, email function or e-fax function for this electronic medical record (EMR).

Further functional aspects of the doctor dashboard are listed below.

TABLE

Example: Doctor View Table - Two Panel

Doctor View
EMR Categories
PMHX Test
Previous Notes
No Notes Entered
Appointment History
Current Notes
Date
Status
Appointment Date
Select Template A four tile format (FIGS. 14A and 14B) are customizable by the user. He or she can change any one or more of the four quadrant views. Alternatively, the user may also choose and customize the screen into a three-tile, a two tile or, if necessary, a one-tile screen in order to focus on one data type. This user's choice is able to be saved for the user based on the "preferences" in the UPP user profile and also to reset back to the default mode of four tiles. The allowed data types are displayed on the right in color blue. The user can simply drag and drop the necessary category of data into any of the quadrant tiles and make them "active" and displayed for that data entry or review or revision.

So, for example, if the user wishes to see images, the previous EMR notes, the pathology report, and to have an area to document notes for the current encounter he/she can do so. If another user wishes to see images, radiology, the past medical history, and the current note, he/she can do that. As indicated above, this screen can be formatted to any number of tiles from 1 to 4.

The doctor view can be converted into a two-tile screen. This allows the user to consume and document as much or as little information in one screen as desired. This format is unique to the program and the work flow is also unique. The archaic way of viewing and documenting information is no longer necessary because any information in the entire cloud-based application is visible and is brought up instantaneously from system 12 via the telecommunications networks. Also, the physician is allowed to build extensive templates in the doctor dashboard.

The following provides examples of functional submodules for the doctor dashboard.

TABLE

Example: Doctor or HCP Pull Down Menu Table

Collapse
Images
Codes
Appointments
Labs
Radiology
Pathology
Current Notes
EMR Categories Summary
Previous Notes
Patient Portal Communication Further, the doctor view can be converted into the one tile format to bring up a custom template and to document the current HC encounter. As indicated before, this section allows the IOS smart phone to instantaneously take an image and permit the user to dictate a note, which is then populated in this section in real time. Any image, document, note, or any data point is accessible in real time via the cloud or through the smart phone or through the Google Glass™ or mobile camera systems. All data is always available at all times anywhere, anytime assuming that security clearance is obtained and the user has the system and method app on the local device.

Section: Pre-Op Pathways—FIG. 24

This is an important part of a surgeon's workflow. Every procedure or operation that is scheduled requires the office to go through a check list of sorts to ensure that all necessary labs, clearances, finances, instruction, and images have been obtained, logged into the system and completed. These pre-op procedures ensure that no pre-condition is skipped prior to the scheduled surgical event. The Pre-Op pathway interactive screen organizes such activities. Documentation that pertains to each operative encounter is stored here and is shown. Designs are provided to allow reminder and tags here that are visible on the IOS or Android™ smart phone device to alert the provider of important things to remember and to which attention should be paid. This is a feature that improves patient safety and efficiency for the provider.

FIG. 24 diagrammatically illustrates the pre-op pathway for the patient layer. Display region 456 provides a drop down menu for a pre-operative check list. Some of these checklists are listed in region 458 including patient name, patient number, type of surgery, facility, anesthesia, surgery date, time and various vital signs such as allergies, diabetic, blood thinners etc.

An example of the pre-op flow chart follows.

TABLE

Example: Work Flow Checklist Table
Test Patient (ID#7)

Age
DOB
Gender
Appointment Date
Appointment Type
Problem Name
Sub Problem Name
Status
Edit Similar to other sections of the cloud-based application, this interactive screen section shows, when a form is filled out with all of the necessary fields, a "complete" indication and by changing color. If the pre-op check list is not filled out properly, the interactive screen will show as "incomplete" and will not change color. To fill out this form, the user clicks the button that says "edit," which brings up this screen that stores the necessary data fields.

TABLE

Example: Sample Pre-Op Workflow Process Table

Pre-Operative Pathways
Patient
Surgery
Suite # 7
Facility
Anesthesia
Surgery Date
Time
Allergies
Diabetic
Blood Thinners
Smoker
Fax Medical Clearance
Phone
Appointment
Fax
Total $
Deposit Collected $
Balance $
Pre Op Appt Date
Post Op Appt Date
Book Or Facility
Anesthesia This interactive screen design is unique in that the further functionality alerts the surgeon to important medications, smoking history, etc, prior to surgery on the smart phone device so that nothing gets missed and the HCP makes safety a priority.

Section: Image Management—Document Management

Image management is one of the several important features of the present invention. In order to maintain the highly secure HC data acquisition and processing, all the data is managed in the cloud-based healthcare data-service system 12. The current trend is to document this photos the condition of the patient. However, the integration of the same into the EMR data has been difficult. In the present invention, this integration, via mobile devices, has been achieved.

Section: Document Manager—FIG. 18

Figure 18:
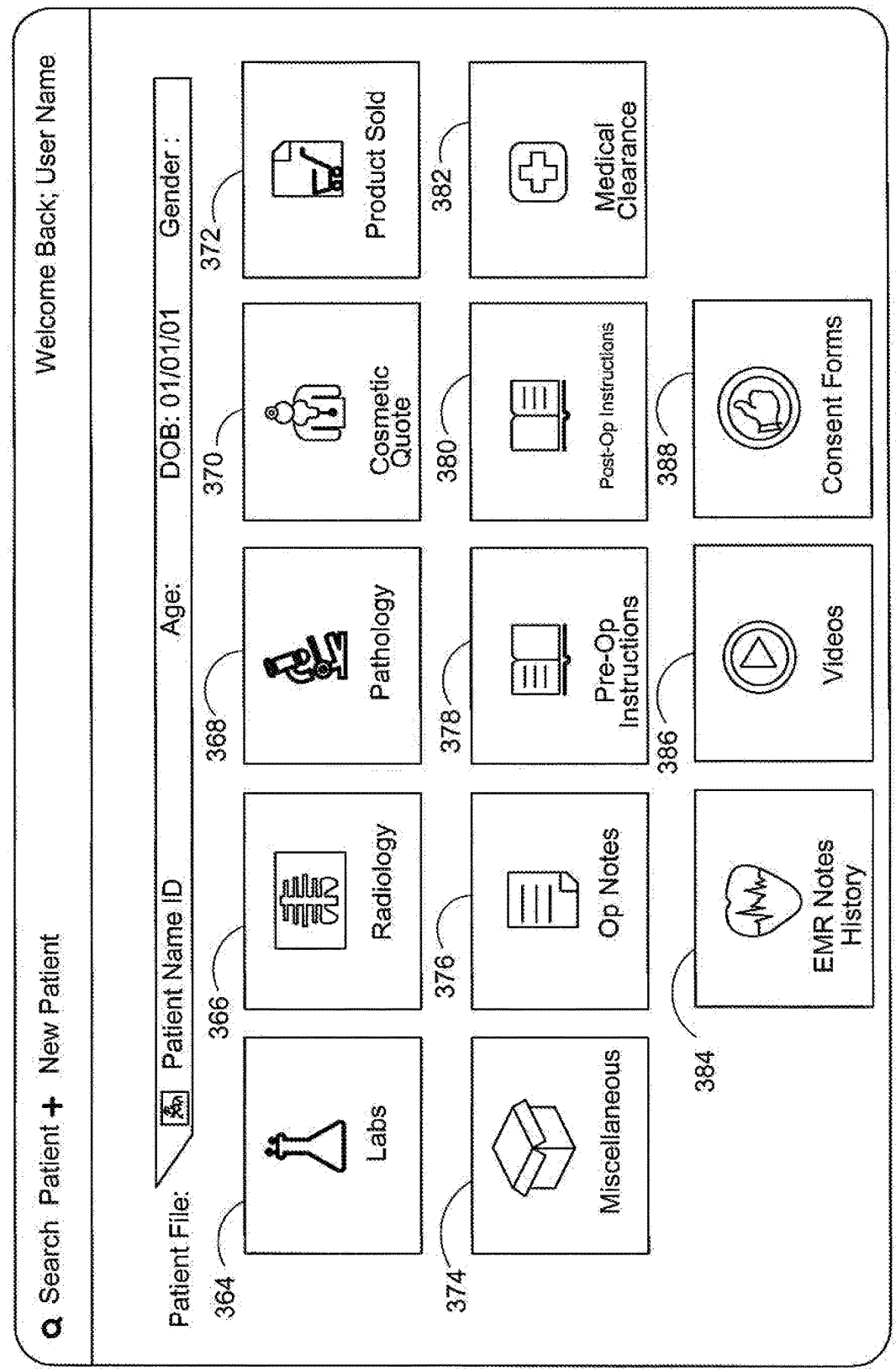
FIG. 18 diagrammatically illustrates a Document Manager (PL).

FIG. 18 diagrammatically illustrates the document manager for the patient layer. From this screen, the user can select lab module 364, radiology module 366, pathology module 368, cosmetic quote module 370, product sold or inventory module 372, miscellaneous module 374, operating notes module 376, pre-op instructions module 378, post-op instructions module 380, medical clearance requirements for a particular patient and procedure at module 382, EMR notes history module 384, video module 386 and consent form module 388.

Section: Image Manager—FIG. 19

Figure 19:
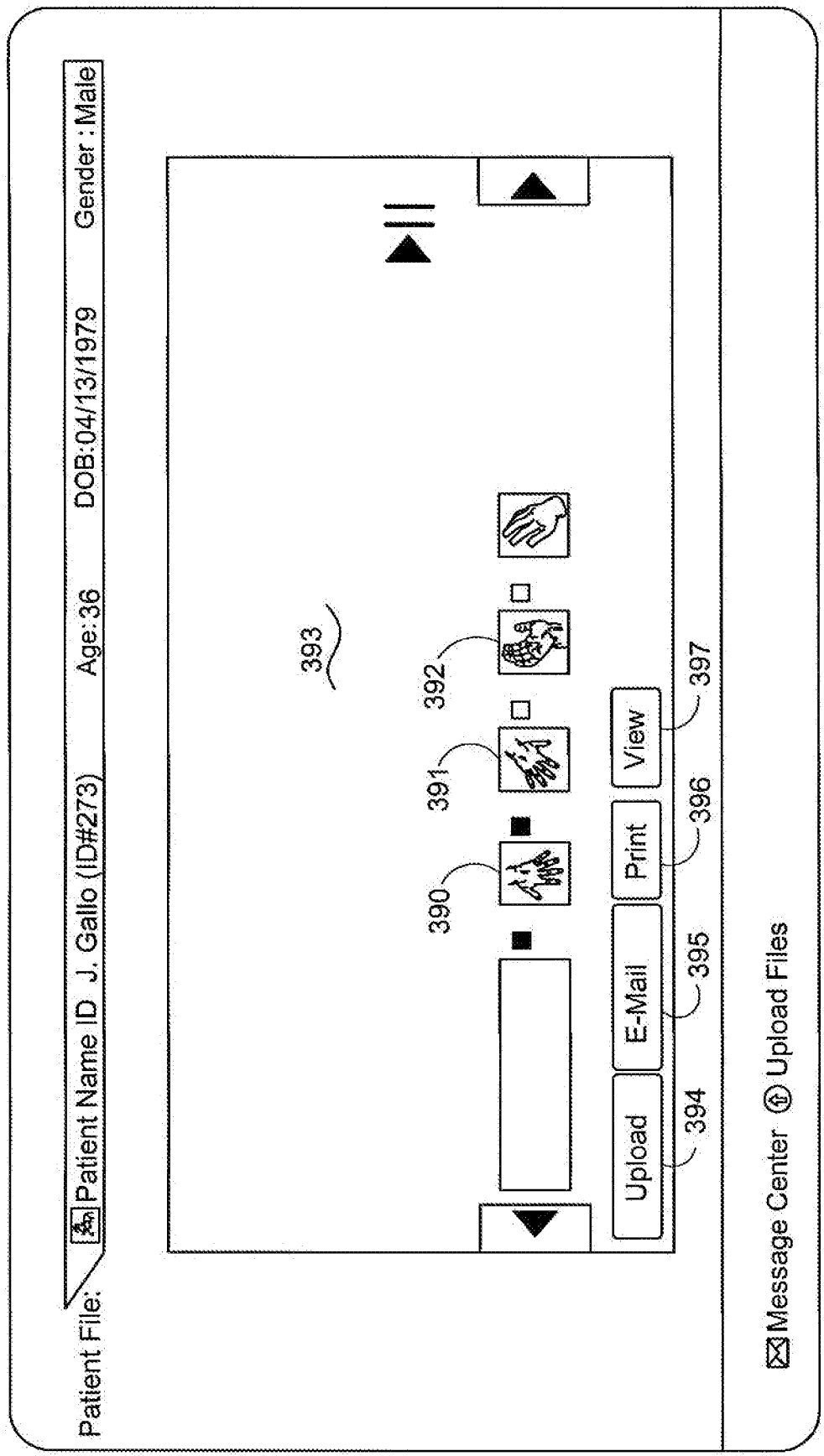

FIG. 19 shows an image manager module for the patient layer. Although region 396 is blank in FIG. 19, the user can select one or more of the thumbnail images 390, 391, 392 (IL 12, 13, 14), those images can be subject of upload function 394, and email function 395, a print function 396 and a view function 397.

Another example of document management follows.

| Table Example: Image Management Table |
|---|
| Test Patient (ID #7) |
| E-Fax |
| Upload |
| E-mail |
| Print |
| View |
| Annotation |

The program functions as an image management software as well. Surgeons have need for taking and sharing many images. As such, many surgeons may use other third-party separate software programs that do not communicate with other software programs. The instant program solves this problem by providing image management within the software. The software platform allows the user to take images with their smart phone application (IOS, Android™, or Google Glass™ or similar mobile camera systems) and automatically, in real time, store that image in the patient folder.

The program provides an area on the Smartphone or the cloud-based web version, to view all patient images, compare two images side by side, annotate on images, and print or email them. The program can also provide appropriate images to the patient and to the referring doctor on their respective apps through a mobile device. In this way, instantaneous access to the necessary images is provided to all of the involved personnel in real time. The system is robust on the mobile platform by leveraging the inherent camera capabilities to an advantage. This way, program eliminates the need for additional hardware such as cameras, video cameras, editing tools, etc. This is also unique functionality. Another unique feature to the program is the use of Google Glass™ as a tool to bring up images and documents and images hands free while in the operating room. This provide another tool for surgeons to utilize and leverage technology to better take care of patients.

The document management system easily organizes documents in respective folders. A unique feature of the program is that it is able to do the organization and upload these documents directly from a user's mobile device to the respective patient chart and the folder from the mobile device in real time. This provides instantaneous access to all such documents to all who have access to the application. Such users are the HC providers, the ancillary HCP staff, the referring doctor, and, of course, the patient.

Section: Cosmetic Quote—FIGS. 20, 21, 22A, 22B and 23

This set of interactive modules enables the provider to prepare customized quotes based on body regions and location where surgery is performed.

Figure 20:
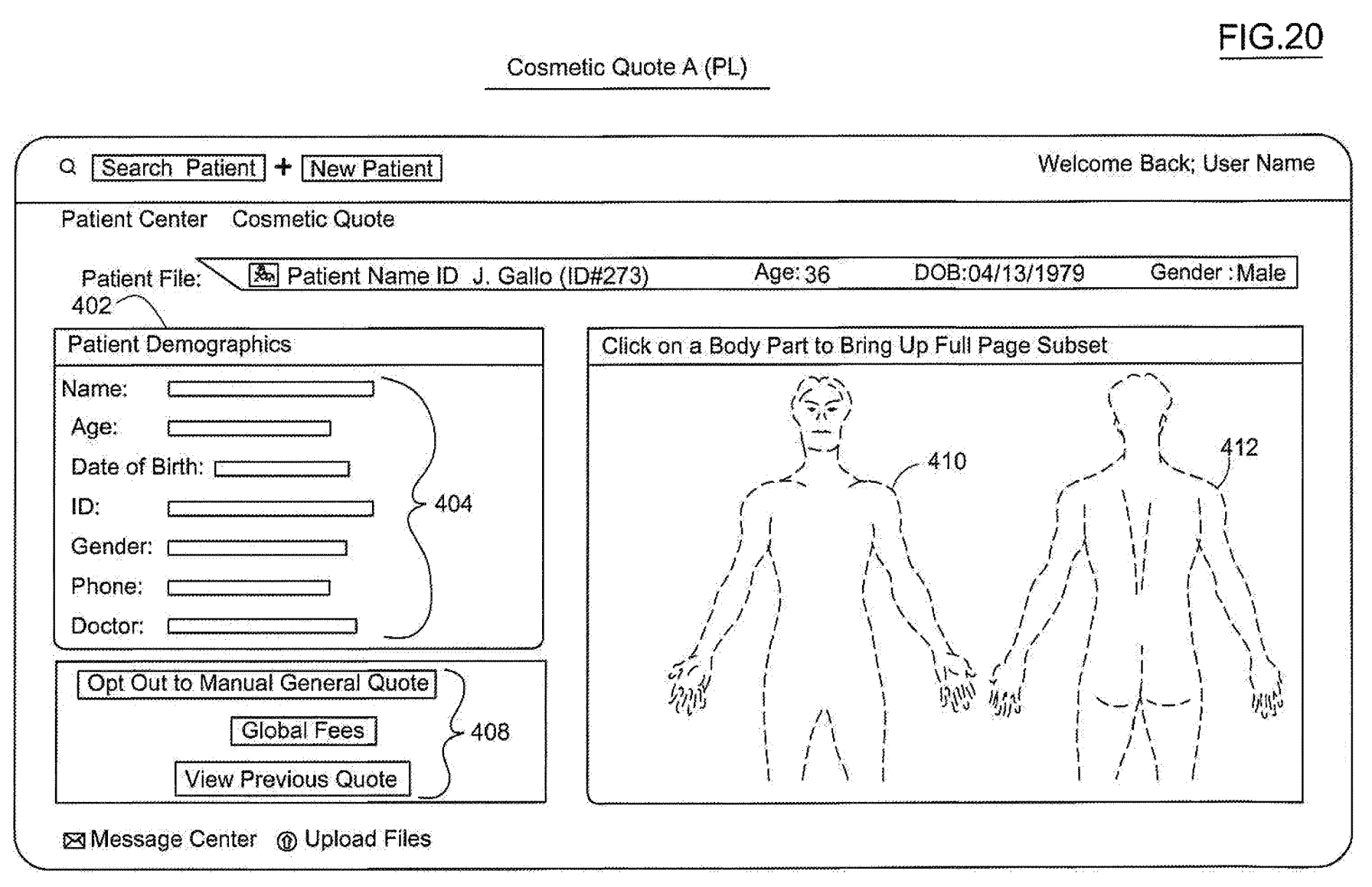

In FIG. 20, cosmetic quote initial screen A is shown. In addition to showing the patient's name, and the user's name, in region 402, patient demographics are shown. The items in region 404 include name, age, date of birth, patient identification number, gender, phone and doctor. In region 408 there is functional selection to opt out to the manual general quote function, to list the global fees function or to view the previous quote for that particular patient. In region 406, a icon image of a patient is shown as posterior and anterior views 410, 412.

FIG. 21 shows cosmetic quote screen B for the patient layer. In region 414 the user has previously selected a body part image. The image appears in 416. The user can select a back button module or function 418 to return to the previous screen. In region 420, the user can select all of the items from a multi presented list. The list region 422 shows a variety of surgical procedures that may apply to that particular patient. The user can select next module function 424.

FIGS. 22A and 22B are to be combined together and diagrammatically illustrate cosmetic quote screen C of the patient layer. This screen is a summary 426 of the previously selected cosmetic events. In region 428 a professional and surgical fees are listed. In region 430 the anesthesia fees are listed. In region 432 the facility and time fees are listed. In row 434 under surgical fees, the number of surgeries is found, the type of procedure, the hours required, the actual cost, a percentages count, the monetary value of the discount, and the total price. Under anesthesia fees column 430 and row 434, the facility is identified, the hour and the time for the surgery and the associated fees. In the facility and time column 432, row 434 shows the facility needed, the time block needed for that surgical operation and the associated fees. Row 440 shows the total of the previous columns. Block 442 identifies miscellaneous fees. Block 444 provides a summary of global surgical fees, global anesthesia fees, global facility and time fees and the global discount. Row 446 shows total amount, a discounted amount and the total amount after discount.

FIG. 23 shows a cosmetic quote D screen. In this screen row 448 shows a total amount paid, whether the payment has been completed and the type of payment. The user is permitted to accept online payments by function module 450 or to note in the system that the patient has made a cash payment at 452.

Another example of the C-quotes is listed below.

| Table Example: Prepare Quotes Per Patient Request Table |
|---|
| Cosmetic Quote |
| Patient Demographics |
| Click on a Body Part to Bring Up Full Page Subset |
| Name |
| Age |
| Date of Birth |
| ID |
| Gender |
| Phone |
| Doctor |
| Ops Out to Manual General Quote |
| Global Fees |
| View Previous Quote |
| Anterior Image Body View |
| Posterior Image Body View |

The image interface allows the user to simply click on the body part and bring up procedures associated with that body part. Then, when a procedure is selected, the user can click through the surgical plan and instantaneously generate a custom quote, which can then be emailed, printed, faxed, or sent directly to the patient app. If necessary, a partial payment or a full payment can be processed directly from here.

| Table Example: Prepare Quote Table 2 |
| --- |
| Close up Body Image |
| Select the Option from multi-select list |
| Select All |
| Price |
| $6,250.00 |
| Select Procedure |
| Abdominoplasty + Flank Liposuction |

The displayed grid demonstrates the ease of use of this module. The user is able to click through the different locations where surgery is performed and different anesthesia groups used and other ancillary charges to be captured in an easy format.

Once this is done, the following table shows a way to capture payments and generate invoices.

| Table Example: Cosmetic Surgery Quote Summary |
| --- |
| Test Patient (ID# 7) |
| Age |
| DOB |
| Gender |
| Cosmetic Summary |
| Anesthesia Fees |
| Procedure |
| Time (hr) |
| Actual Cost ($) |
| Discount ($) |
| % |
| Value ($) |
| Price |
| Facility |
| Time(hr) |
| Fees ($) |
| Facility |
| Time (hr) |
| Fees ($) |
| Upper or Lower Blepharoplasty (eyelids) |
| Miscellaneous Fees |
| Procedure Name |
| Fees ($) |
| Add |
| Global Surgery Fees |
| Global Anesthesia Fees |
| Global Facility & Time Fees |
| Global Discount |

A payment processing portal directly communicates with PayPal™ processor software to process the transaction. Alternatively, the patient can also use their mobile app to connect up to PayPal™ and process the transaction and keep a record of the transaction.

The present cloud-based healthcare data-service system and method gives unprecedented access to the patient that has not been previously available. The agnostic aspects of the system and method, closely tied to the security of all data made available to the mobile devices, is unique and greatly opens up and makes accessible a wide range of HC data to the patient.

Also indicated earlier, this module interacts with the system administrative dashboard to manage the facilities, anesthesia groups and charges as shown below.

| Table Example: Admin Dashboard |
| --- |
| Cosmetic Management |
| Manage Procedures |
| Manage Miscellaneous |
| Manage Facility & Time |

Section: Schedule Appointment From Patient Layer—FIG. 27

FIG. 27 describes, for the patient layer, a schedule appointment. By activating schedule appointment region 468, in region 470, the user can identify the status (pending/not pending), the patient name (from a pull down menu list), the location of the patient, the start date and time, the appointment time, the type of appointment (follow-up, new consultation, surgery) the type of problem (also a pull down menu) and existing insurance. Notes region 472 permits the user to add notes to that particular appointment schedule. The region 471 prompts the user to identify whether the appointment has been confirmed or not. In region 474 certain additional information is provided such as the treating physician, the end date and time, the appointment purpose, the sub-problem, and eligibility status. The user can save an exit function 476, save and go to patient record 478, exit function 480 or go to patient dashboard function 482.

Section: Message Center—FIG. 28

FIG. 28 diagrammatically shows the interactive display screen for the message center. Function block 484 permits the user to go to the home page and function block 486 permits the user to go to a message center. The message center can be an inter office email system or an active chat box or a more formal email communications system. The message center permits the user to select in box function 488, sent function 490, compose function 492, and message document function 494. Region 496 identifies who sent the message and the subject of the message and the date.

Section: Mobile Platform—Generally

The mobile platform has four native apps designed for IOS devices and Android™ devices alike. In addition, a native application is provided for using the Google Glass™ through the system and the program. The following Table lists four key apps.

| Mobile Platform App Table |
| --- |
| The provider/physician app |
| The patient app |
| The staff app |
| The referring doctor app |
| The Google glass app |

Section: Doctor or HCP Provider Apps

When a provider first downloads the provider app onto a mobile device, he/she has to go through a registration process. All communication is heavily encrypted at the coding level to the network level to the hosting level and all intermediate areas.

Section: Mobile Doctor Home Screen—FIG. 29

FIG. 29 diagrammatically illustrates the mobile doctor home screen which is presented either on an Apple™ smart phone with an IOS operating system or an android smart phone. The cloud based system 12 delivers the data as objects and permits the user (after the user has entered his or her password or biometric security code) to access the information from the cloud based server 12 in accordance any permissions or roles established by the administrator of system 12. From the doctor home screen, the physician can conduct a patient search 502 or add a new patient by touching functional block region 504. Otherwise, the doctor can request from the cloud based system 12 the current patient schedules by activating touch screen region 506, open a module manage documents by selecting region 508, open patient information at region 510, select his or her surgical schedule by activating region 512, manage images by selecting region 514, or activating the inventory module 516.

It can appreciated that the cloud based server system 12 is activated by the user on the mobile device selecting an APP on the smart phone. Upon selection of the APP and confirmation of the security code, the person on the mobile device selects an item and a request is presented to the cloud based system 12. The server in the cloud based system 12 then responds by downloading data objects to the mobile device.

Section: Mobile Patient Layer (Doctor Access)—FIG. 30

Figure 30:
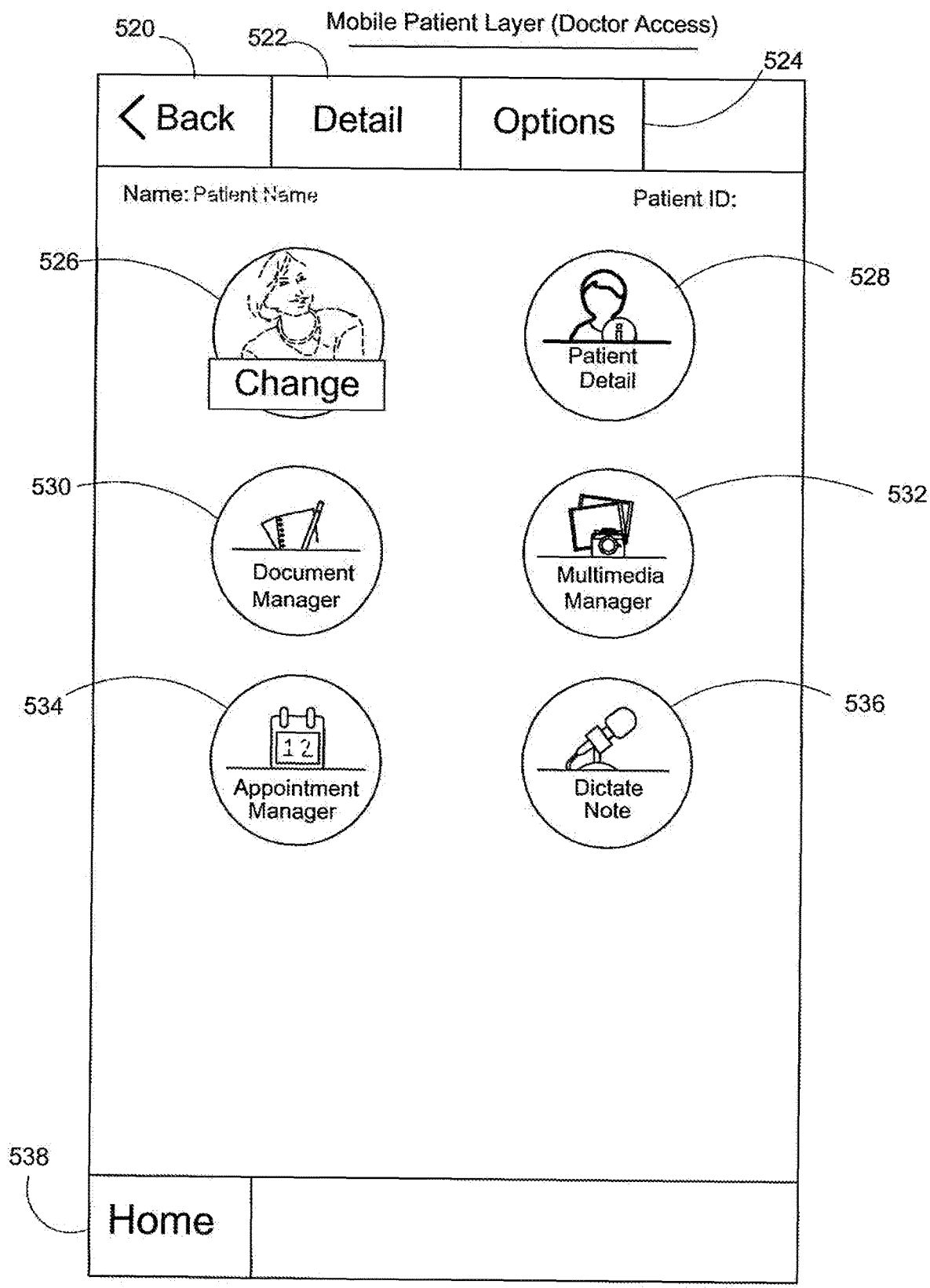
FIG. 30 diagrammatically illustrates a Mobile Patient Layer (Doctor Access)(see Doctor or HCP Provider App Section).

FIG. 30 diagrammatically illustrates a mobile patient layer and a doctor access to the mobile patient layer. After selecting and inputting the security code and after the cloud based system 12 approves the security code, the physician can select the back button by selecting touch region 520 on his or her smart phone, can request more details on the patient by selecting region 522, or can provide options by selecting 524. The options button would generate a pull menu permitting the doctor to view any particular item in the patient file. For example, the item listed in the doctor manager FIG. 18 may be listed in the pull down menu from options selection 524. Region 526 can be a photograph or image of the patient. Region 528 permits the doctor using the APP to select more patient detail. Region 530 selects the document manager module, region 532 selects the multimedia manager, region 534 selects the appointment manager module and region 536 permits the physician to open a module in the APP to dictate a note and create an audio file within the APP. As indicated earlier, the audio file can be converted or translated with a voice recognition module into text. The text is stored in the patient detail area. For example, the text generated from the speech recognition module would be automatically input into EMR new notes region 290 and specifically text region 295 discussed earlier in connection with FIG. 14A. After the physician completes the audio input as a dictated note, he or she may edit the note as discussed above in connection with FIG. 14A and the editing tools. These editing tools would also be downloaded as an APP into the physician mobile device. When the physician selects save notes function 296, the APP (i) uploads the voice to text into the cloud based system 12 and (ii) deletes any audio record and any text record from the memory of the mobile device or local device.

Section: Mobile Healthcare Provider HCP Schedule—FIG. 31

Figure 31:
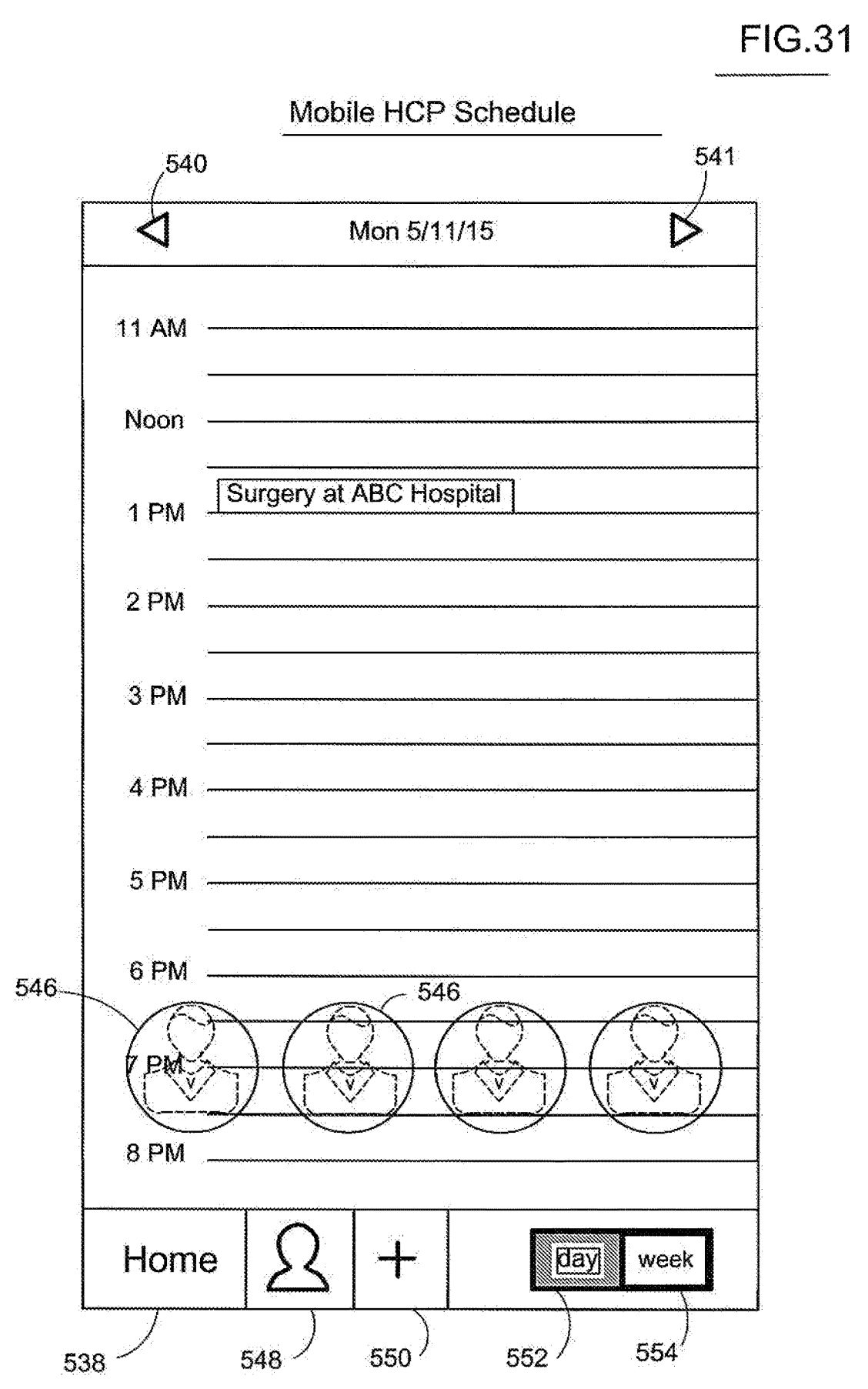

FIG. 31 diagrammatically illustrates the mobile healthcare provider HCP schedule. As shown in FIG. 31, the physician can move back a screen to the earlier presented display by selection of back button function 540. The physician can move forward to another screen by selection of forward button function 541. In column 542, the screen is segmented by time markers. At time marker 12:30-1:00 PM, the physician viewing the screen in FIG. 31 notes that he or she has surgery at a hospital. This display is presented in display region 544. Additional displays may be presented on display screen FIG. 31 as discussed later in conjunction with the search call scheduling processes. On the lower portion of the screen in FIG. 31, a plurality of images for HCP images 546 and 547, quickly remind the physician other HCP who have notes or appointments on the schedule. The healthcare provider HCP can select home button by function 538, can select a particular person by selection function 548. By selecting person 548, a pop-up menu could be provided which permits the physician to identify one of a plurality of HCP such that the physician can then view that selected HCP's schedule for that day. By selection of function 550, the user can add a new scheduling event to the HCP schedule. Functional buttons 552 and 554 permit the physician to select a daily schedule or weekly schedule. In addition, not shown in FIG. 31, is a "save" function which permits the physician to add and save scheduling event data to the schedule.

Section: Mobile HCP Patient Assessment—FIG. 33

Figure 33:
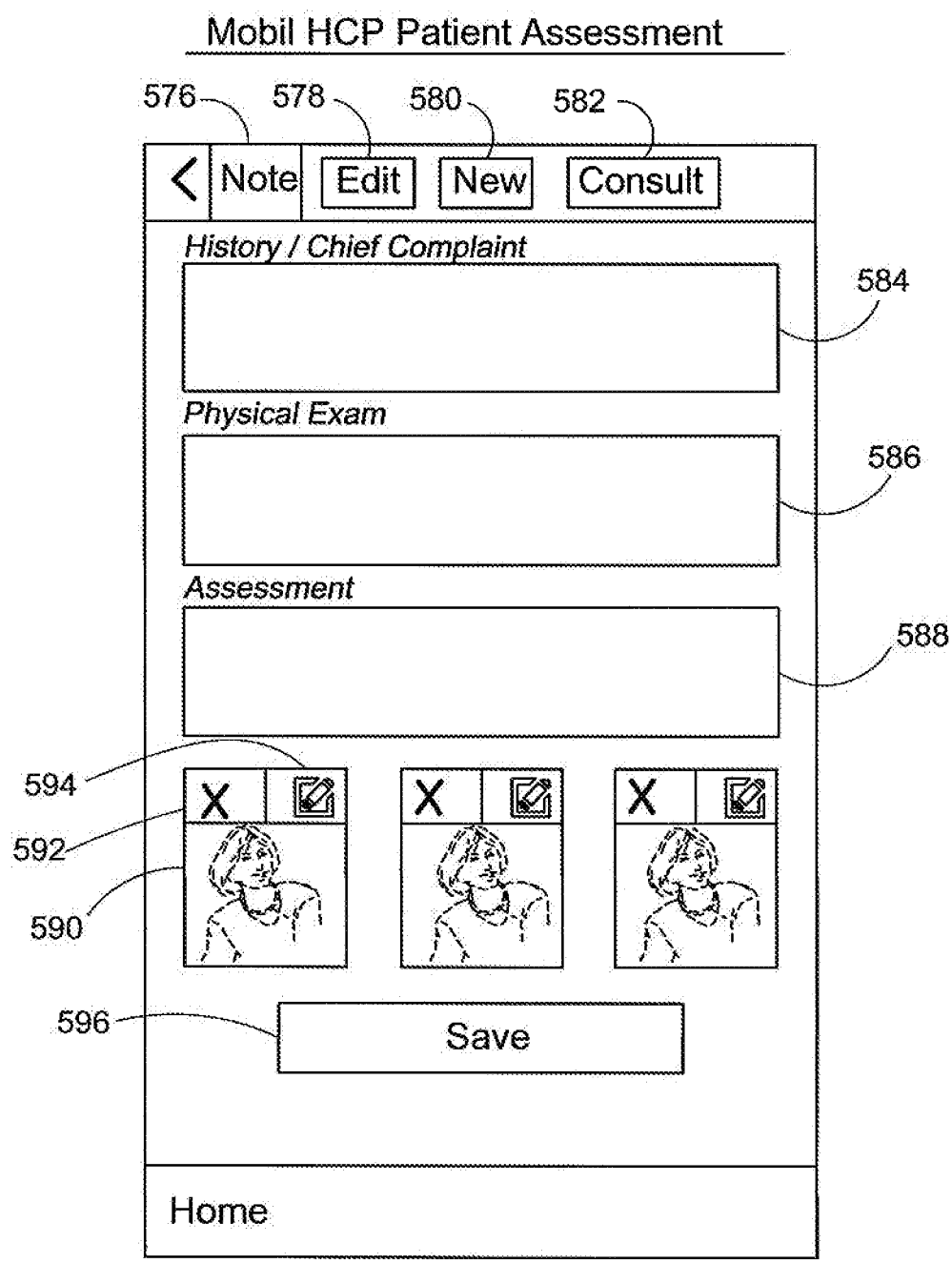
FIG. 33 diagrammatically illustrates a Mobile Doctor or Health Care Professional ("HCP") Patient Assessment screen (see Doctor or HCP Provider App Section).

FIG. 33 diagrammatically illustrates the display screen on a mobile HCP device which permits the HCP to input certain patient data. By selecting functional display block 576, the physician activates the "note" function permitting the physician to either input data into regions 584, 586 or 588 via the keypad. Alternatively, a "dictate" function block could be added to FIG. 33 permitting the HCP to input an audio record into one of the particular regions. This audio record would be translated into text and inserted into history/chief complaint data block 584, physical exam data block 586, or assessment data block 588.

By selecting edit function 578, the physician could edit any of the textual blocks 584, 586, 588 via the keypad on the mobile device. The keypad would appear upon activation of edit function 578. By selecting "new" function 580, the physician would clear the screen and be presented with a new screen. Upon selecting "new", the APP would upload the data to the cloud based system 12 and, generally simultaneously, delete any data in the memory on the mobile device. In this manner, all the data is secured on the cloud based system 12 and not inadvertently saved on the mobile device. Without saving any of the data on the mobile device, if the mobile device is lost or stolen, the highly secured nature of the health data acquired by the HCP and the mobile device is not exposed to the robber or the other person who discovers the lost mobile device.

Selection of consult function 582 would permit the user to select one or more protocols or templates for a particular patient. For example, if a physician's assistant was utilizing the mobile device, and the patient was a new patient, the consult button menu would show, among other things, a section called "vitals." By selecting vitals from the template menu, a list of questions would be presented to the physician's assistant. The assistant would make inquiries of the patient and complete the vitals category. Additionally, the physician's assistant would take blood pressure and record the blood pressure into the mobile device.

Another function of the mobile HCP patient assessment is the use of photographs or images one of which is identified as image 590 in FIG. 33. In this manner, the APP on the HCP mobile device can capture an image with a camera on the mobile device and show that image in the patient assessment module. By selecting delete function 592, the image is deleted not only from the APP memory but also from the local memory in the camera. By selecting the marker module 594, the HCP can alter or mark the image to point out a particular area of concern identified by the patient. Save function 596 saves all the data from the HCP input and uploads that data to the cloud based system 12. At the same time, all the data is deleted from the memory of the local device.

Section: Mobile Image Process—FIG. 34

Figure 34:
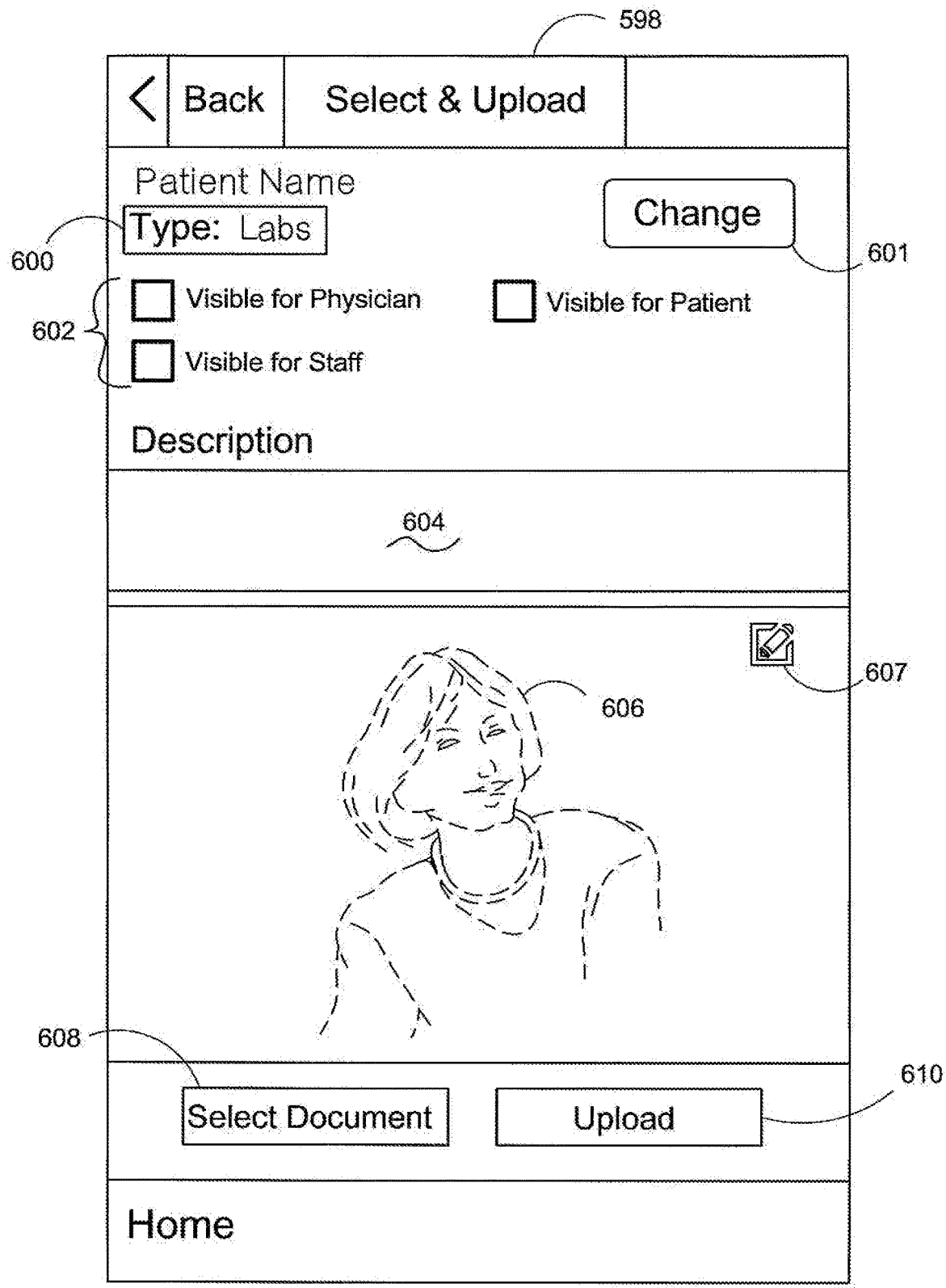
FIGS. 34 and 35 diagrammatically illustrate Mobile Image Processes (see Doctor or HCP Provider App Section).

FIG. 34 diagrammatically illustrates a mobile image process. As indicated earlier, the user can go back a screen. When the user selects back function, the APP requests information from the cloud based server 12 and the server downloads that information from the previous screen back to the mobile device. Alternatively, the local device memory has the previous screen data stored in temporary memory. By selecting "select and upload" function 598, the user with the mobile image processing can upload the data to the cloud based server 12. The user can identify the type of data viewed as by text keypad input in region 600. Further, the user can check off or select the permissions for the image by selecting any one of the items in region 602 such as visible for physician, visible for staff or visible for patient. Of course, the HCP could select all three of these items. The HCP can input via keypad text a description of this situation in region 604 or permit an audio input which is converted to text. Image 606 can be captured by the HCP using the mobile device. Marker 607 can be used to highlight or circle any problems. The selection of touch screen region 608 permits the user to select any particular document. Upload function 610 permits the user to upload all the information from the mobile image processing screen to the cloud based server. Upon upload, the local memory in the mobile device is deleted. The deletion may occur when the HCP closes the App or the App times-out and closes automatically. The "delete acquired data in memory" may be substantially simultaneous with the upload or somewhat later with an "APP Closed" or time-out function.

Section: Mobile Image Process—FIG. 35

Figure 35:
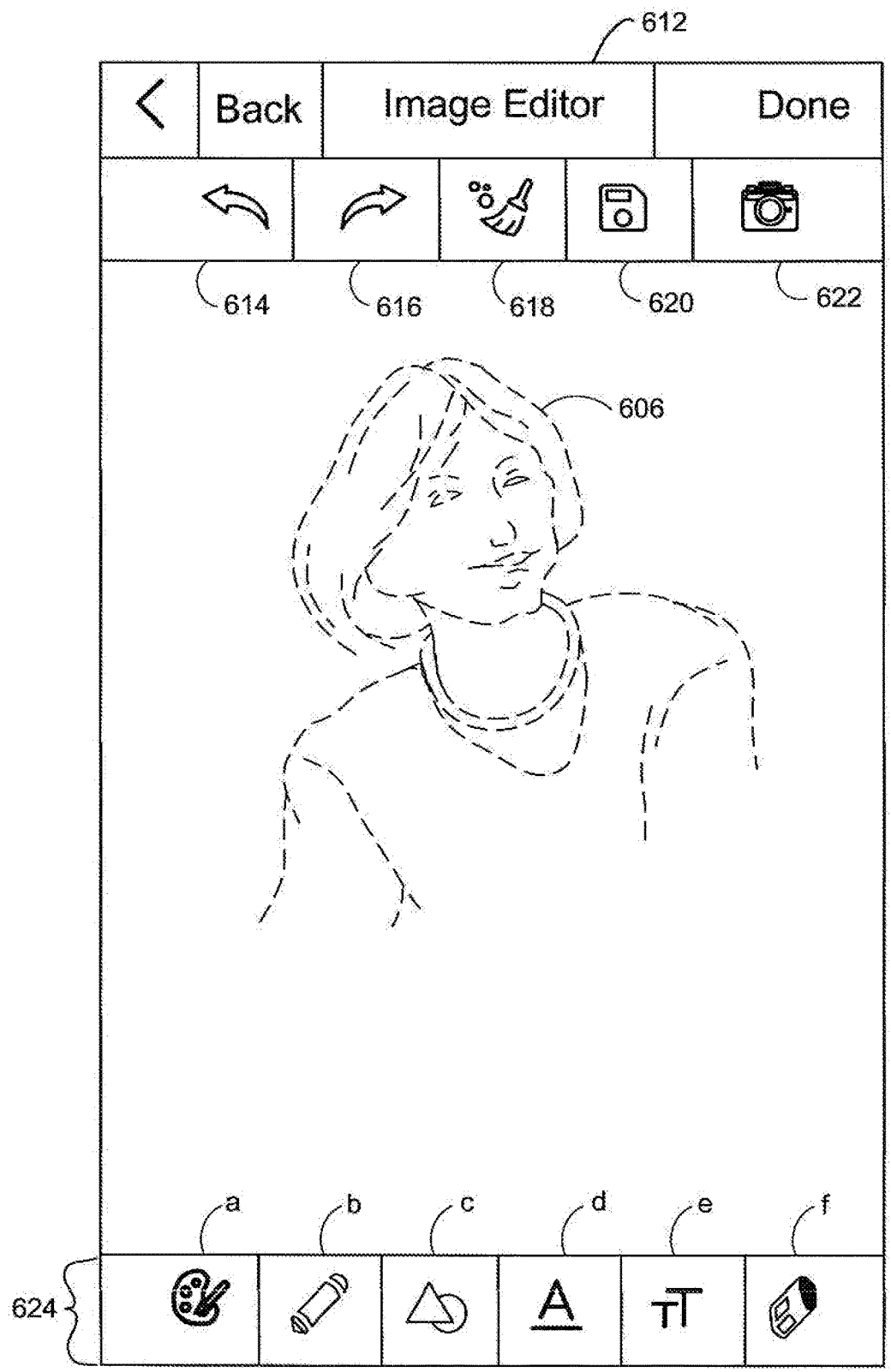

FIG. 35 diagrammatically illustrates the mobile image processing B. In this process, the user has selected image editor function 612. This image editor includes a group of somewhat standard image editing aspect including undo function 614, replace or reinsert function 616, erase function 618, save function 620 and activate camera function 622. Image 606 can be edited in this manner. Additional editing items are shown in row 624. By selection of 624a, the user can select one or more color pallets and color certain items on image 606. Function b permits the user to highlight certain portions on image 606. Function c permits the user to circle or select a triangle region over image 606. Function d permits to activate a typewriter function to type information on image 606. Function e changes the size of the type and function f is an eraser to erase text or lines.

Once logged on, the user then sees the interactive having the functions and data listed below. This is an example of the HCP mobile home screen.

| Table Example: HCP Ap Menu Selection |
| --- |
| Welcome HCP Bob |
| Logout |
| Patient Search |
| Scheduler |
| Clinic Module |
| Add Patient |
| Communication |
| Widget |
| Document Manager |
| Photo Manager |
| Surgery Appointment |

The home screen allows the user to engage in different activities as needed. This screen allows the user to quickly create a patient chart, schedule an appointment, create a note, take an image, upload a document and convert it into a PDF, and many other activities. A unique feature is to use a PDF conversion tool to quickly take an image of a document through the app and instantaneously convert it into a PDF document and upload it to the patient chart and appropriate folder directly through the mobile app. To do this, an app referred to as the turbo scanner runs through a widget section of the program. The program also interfaces with emails as well uploads any attachments in the email directly into the app. No longer is it necessary to open, print, scan, and upload and create inefficiencies associated with these functions. This process is truly paperless. Also enabled, right on the screen, is a user control that allows access to images and documents to different users such as the patient, physician, etc. Also images can be directly uploaded into a preformatted template if necessary. The control is provided here to choose the image to either be stored in the image management section of the patient chart or directly be stored in the encounter note.

The following table shows another example of functional elements for the HCP mobile application.

| Table Example: Document Manager Table |
| --- |
| Carosel of Mini-Images |
| Selected large Image |
| Patient Name |
| Home - Search - Labs |

| Table Example: Document Select And Upload Table |
| --- |
| Patient Name |
| Type (Labs, etc.) |
| Visible to HCP (pull down menu HCPs) |
| Send to Patient |
| Select - Upload |

Some of the other functional screen modules are shown below.

| Table Example: Appointment Detail Table for HCP |
| --- |
| Appointment Detail |
| Patient Name |
| Physician Name |
| Type |
| Status Name |
| Problem |
| Sub Problem |
| Reason |
| Location Name |
| Start Date |
| End Date |
| Home |
| Search |

The mobile application unique performs many functions. In the clinic, with the module of the "provider app," the user is able to open images, documents, appointment details, and also record a note that will be directly ported into the cloud-based web chart. Not only can the physician record a note, the physician can also assign CPT, ICD and Modifier insurance codes to captures additional billing charges.

| Table Example: HCP Mobile Ap Menu Screen |
| --- |
| Name |
| DOB |
| Patient ID: 8 |
| Patient Detail |
| Document Manager |
| Photo Manager |
| Appointment Manager |
| Record Note |
| Home |
| Search |

In addition, the physician can also take images and instantaneously use them in the encounter note. The image collection and storage and documentation are unique to the electronic record software disclosed herein.

Because all of the data is accessible through the mobile device, the users are able to access through the secure encrypted network in real time anytime, anyplace. The program also leverages many of the inherent capabilities of these devices. The consultation is instantaneously converted into a multimedia presentation through the use of Apple TV™. The hardware setup is easy and convenient as well. With the use of simple modern TV monitors with HDMI connectors, a mobile device, such as a smart phone (IOS) and Apple TV™, the program is able to instantly use this to share and present information to patients in a multimedia format. No longer is the user required to sit at a computer screen, hold tablets, and/or look away and share paper. The user can actually use their own mobile device to bring up any data point and use the airplay/mirroring capabilities of the device to show the content to the patient and families on a television monitor, for example. This convert a passive consultation into a real interactive consultation. When the power of the patient app is added to this situation, true interactivity between the patient and the physician and the entire office is provided.

Section: Doctor Mobile Schedule; Surgical Schedule Module FIG. 4

The surgical scheduler module presents an extremely functional tool to the HCP. Although scheduling software is well known, the additional functionality added by the cloud-based healthcare data-service system and method is unique.

Figure 4:
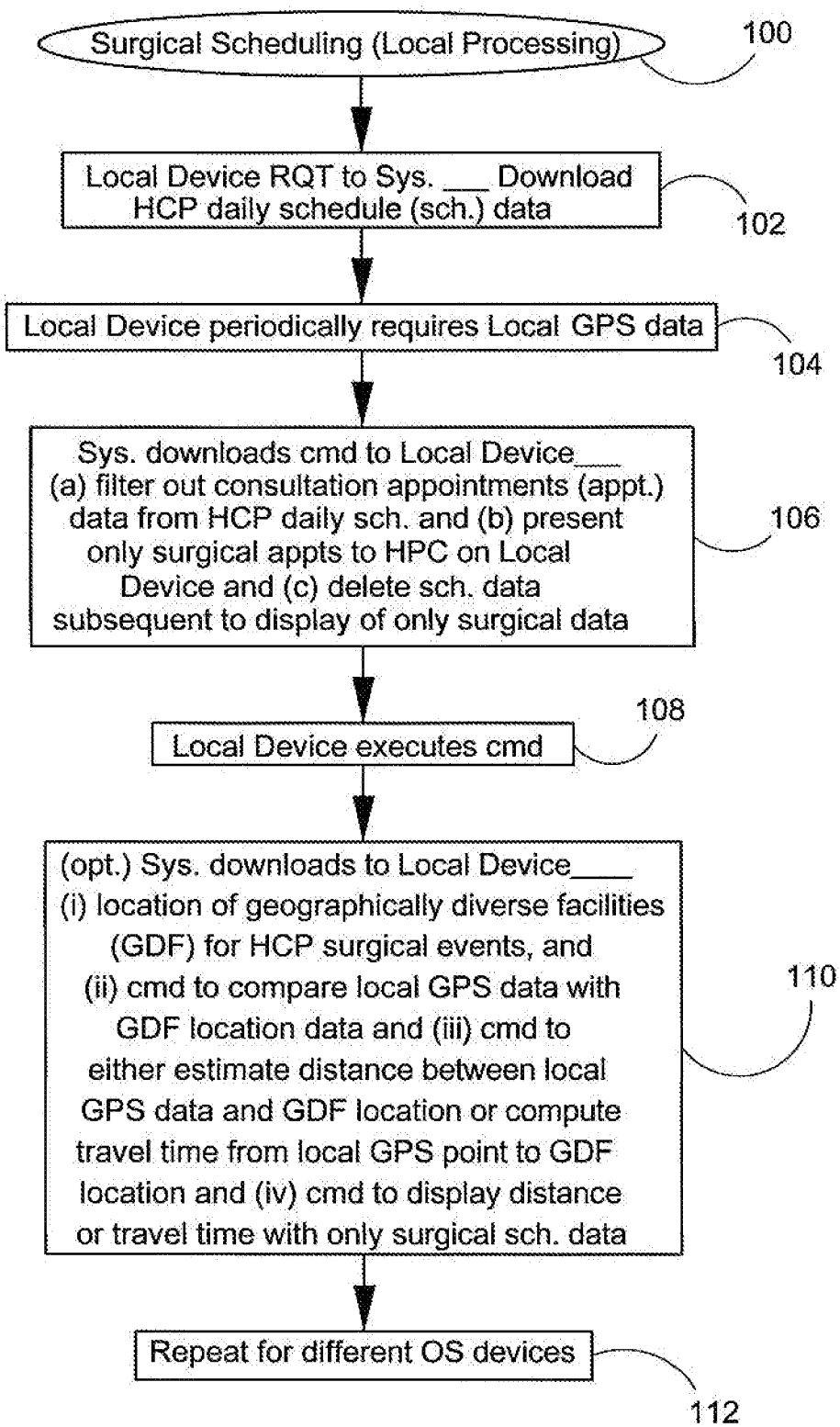
FIG. 4 diagrammatically illustrates a Surgical Scheduling (Local Processing) flow chart.

FIG. 4 diagrammatically and generally describes a flowchart for surgical scheduling based upon local processing by the local device. The surgical scheduling program 100 is initiated in step 102 with a local device request to the system, requesting the system to download the healthcare provider HCP's daily schedule into the local device carried by the healthcare provider. Of course, if the HCP is in his or her office using a desktop computer, the schedule can be downloaded from cloud computing system 12 into the desktop. In step 104, the local device periodically requires the local GPS data. The local GPS data is acquired if the HCP is using a mobile device. In step 106, the system 12 downloads a command to the local device which (a) filters out consultation appointments data from the HCP daily schedule and (b) presents only surgical appointments to the HCP on the local device. Further, the cloud based system 12 downloads a command which delete the schedule data subsequent to the display of "only surgical data." In step 108, the local device executes the command In optional step 110, the system downloads to the local device the location of geographically diverse facilities (GDF) for the HCP surgical events which are then currently listed on the HCP daily schedule. Also, the cloud based system 12 downloads the command which compared the locally obtained GPS data with the geographically diverse facility data GDF location data. The cloud based system 12 further downloads a command which either estimate the distance between the current location obtained from the GPS data and the GDF location or computes travel time from the local GPS to the GDF location. The system further downloads a command causing the local device to display distance or travel time with the "only surgical schedule data." In step 112, the system repeats for different operating system OS devices.

The initial screens are discussed above. The program and method allows GPS location services to also be used on the local device. This allows the user to employ the part of the program that is geo-specific to further streamline workflow. An example of such functionality is that the mobile device recognizes the geo location and only brings up the schedule pertinent to that location, so that the provider can easily look through that part and not have to parse through a very long and busy looking schedule.

Section: Surgical Scheduling (Central Processing)—FIG. 5

Figure 5:
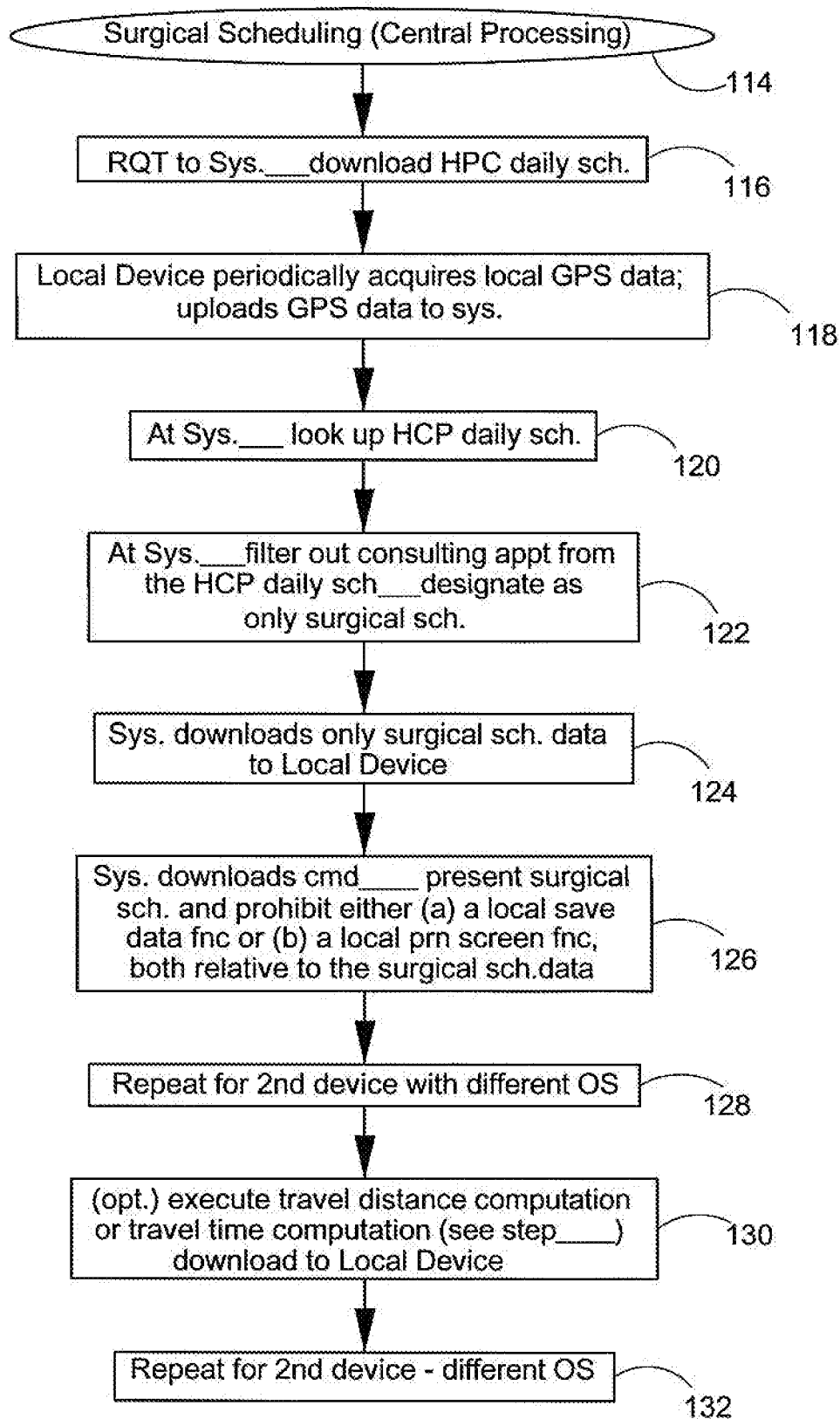

A surgical scheduling flowchart, from the perspective of central processing cloud based system 12, is shown as process 114 in FIG. 5. In step 116, a request is presented to cloud based system 12 to download the healthcare provider HCP daily schedule into the local device. In step 118, the local device periodically requires local GPS data and uploads the GPS data into cloud based system 12. At the system in step 120, the program looks up or gathers the HCP daily schedule. This HCP daily schedule includes surgical events as well as consultation. In step 122, also at cloud based system 12, the processor filters out consulting appointments from the HCP daily schedule. The resulting filter daily schedule is designated as "only surgical schedule." In step 124, the system downloads the "only surgical schedule" data to the local device. In step 126, the system also downloads a command to present the surgical schedule to the physician at the local device and prohibit either (a) a local save data function or (b) a local print screen function, both relative to the surgical schedule data. In step 128, the process is repeated for second device having a different OS. In step 130, an optional step is recognized to execute a travel distance computation or travel time computation as discussed earlier in connection with step 110 in FIG. 4. The resulting travel distance or travel time is then downloaded to the local device. In step 132, the flowchart is executed for the second device having a different OS.

Section: Surgical Scheduler Flowchart—FIG. 32

Figure 32:
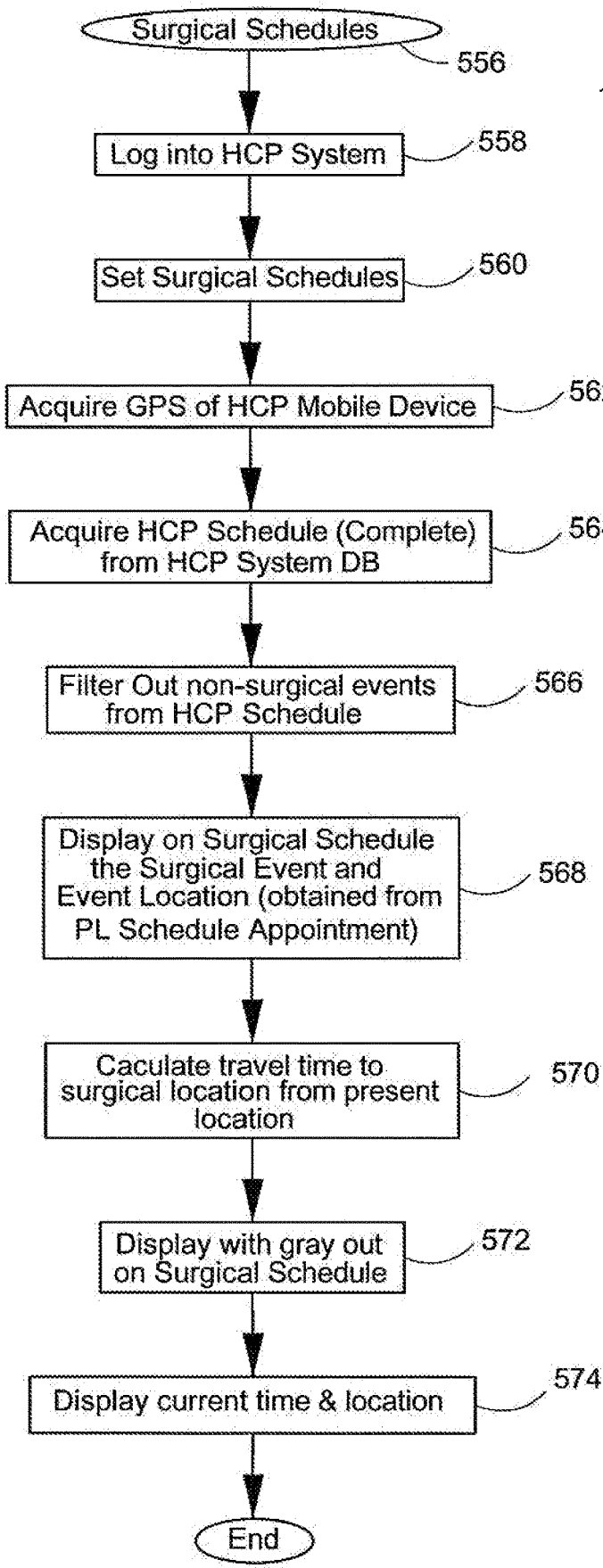
FIG. 32 diagrammatically illustrates a Surgical Scheduler Module (see Doctor or HCP Provider App Section).

FIG. 32 diagrammatically illustrates a surgical scheduler program 556 which permits the HCP to view both the full schedule as well as the particular schedule for a person HCP or a facility where the surgery will occur. In step 558, the user logs into the cloud based system 12 in particularly the HCP system. In step 560, the healthcare provider HCP selects surgical schedules to be presented on his or her mobile device or on the desktop unit. Step 562 acquires the current location of the HCP mobile device. Step 564 acquires the HCP schedule from the cloud based server system 12 and more particularly from the HCP system database. Step 566 filters out the non surgical events from the HCP schedule. Step 568 displays on the surgical schedule only the surgical event in the surgical event location. This is obtained from the patient layer (PL) schedule appointment module. In step 570, the mobile device calculates the travel time to the surgical location from the present location. Alternatively, the mobile device could compute the distance from the current GPS location of the mobile device to the schedule surgical location. Step 572 displays on the "surgery only" display the travel time in a gray out presentation. In this manner, the HCP is prompted to go to the surgical location at the appointed time. Step 574 displays the current time and location on the mobile device thereby giving the HCP an indication how close or far away the HCP is to the surgical device and the projected time of arrival. This is helpful in order to coordinate the surgical event with other HCPs at the surgical site.

Section: Patient App—Mobile Patient Home Screen FIG. 36

Patient access to their own medical records has been an issue for decades. The present system and method, after the system clears the security of the patient's mobile or desktop device, revolutionizes telemedicine, increases portability and introduces interactivity between the physician and the patient.

Figure 36:
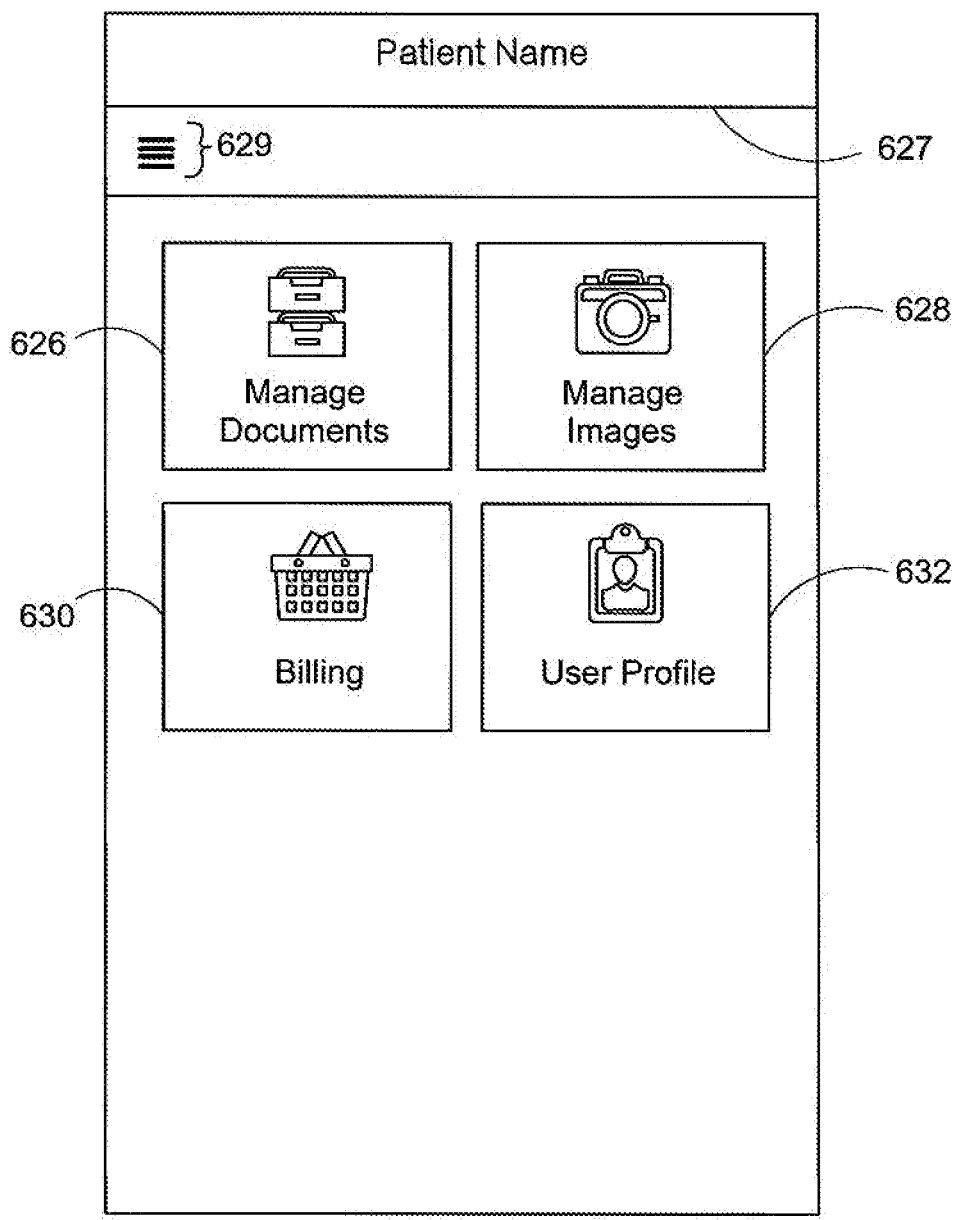
FIG. 36 diagrammatically illustrates a Mobile Patient Home Screen (see Patient App Section).

FIG. 36 diagrammatically illustrates the patient home screen wherein the patient can establish a digital access to the cloud based system 12. In region 627, the patient name and identification number is displayed. Prior to display of mobile patient home screen, the patient has activated an APP on the patient's mobile device and has input his or her security code and/or biometric information into the APP. The APP then forwards that information to the cloud based system 12 which approves/disapproves of the security code clearance. If approved, the patient home screen is displayed on the user's device. Bars 629 represent an active a pull down menu for various other interactive display screens that the patient can access. For example, the patient may want to access his or her blood lab work from the previous visit to the physician. By selecting lab work in pull down menu 629, the lab work results would be presented to the patient. By selecting region 626, the patient can manage documents. By selecting region 628, the patient can manage images. By selecting region 630, the patient can view the current status of bills owed to the HCP and/or payments made to the HCP. Region 632 permits the patient to alter his or her user profile.

The following is a further example of the patient mobile module.

| Table Example: Patient Ap Menu Screen |
|---|
| Welcome Patient Bob |
| Logout |
| Communication |
| Documents |
| Images |
| Social |
| Billing |
| Web Checkin |
| Patient Education |
| User Profile |
| Settings |

As shown above, significant functionality is provided to the patient. Through the patient app, which can be downloaded once a patient creates an appointment, he/she can communicate to the office through the app, perform web check-in for appointments, view patient educational materials (including preoperative and post operative instructions), view procedural video and or images, view invoices and bills and pay them, instantly post reviews or comments on social media sites such as Facebook™, Google Plus™, and Twitter™, view pertinent images, and review documents. This allows the patient to have access to his/her medical information at all times anytime, anywhere. This app also allows synchronizes with a native calendar application on the device such as iCal™ and Google Calendar™ to remind them of their appointments. In addition, emails are sent to confirm appointments.

| Table Example: Patient Ap Menu Table (Post Icon Selection) |
|---|
| Welcome HCP Name |
| Logout |
| Communication |
| Documents |
| Images |
| Social |
| Billing |
| Web Checkin |
| Patient Education |
| User Profile |
| Settings |

Section: Staff App

The staff app is a version of the HCP or Doctor App with limitation for the administrator or the assistant to assist in patient care. This allows the staff user to upload images in the room, upload documents in the room, search through records, and perform other functions so that efficiency is gained. No longer will the staff have to leave the room to use a fax machine, a scanner, or any other hardware to work with a patient.

Section: Referring—Related HCP—Doctor App

The referring doctor app is a unique feature of the program. Often there is need for physicians to get multiple faxes, emails, papers, images, and other materials from referring physicians or doctors who provide related HC work to the patient. In addition, many times, letters are written back and forth to the referring physician. This app solves the problems associated with such communications. Through the use of the referring doctor app that is tracked with the unique NPI number, the user is able to allow access to the pertinent patient data in real time to the referring doctors. There is no longer a need to mail or fax papers or documents. Through the referring doctor app, the user can simply open the chart of the patient and view it or import it and print it out or save it as desired. This creates a tremendous amount of efficiency in the process and is truly unique. This functionality also allows real time access because, once anything is in the database, it becomes instantly accessible to all users.

Section: Google Glass™ and Other Wearable Technology Interface

The interface to Glass™ and other mobile camera systems is unique to the cloud-based healthcare data-service system and method. Google Glass™ nor the smart watch been part of an electronic health record system. Now, such mobile devices are integrated directly into the program. The workflow enables the surgeon to do hands-free work while in the operating room or other situations where hands-free technology is beneficial. Such situations include the operating room, where a surgeon has to review a document prior to surgery or recall an image or an x-ray, and, in other cases, to capture an image for documentation purposes. Now, the program allows the user to directly bring up a patient chart to view image and or documents, and to also upload the same directly into the charts. This is an extraordinary feature that is unique. The program can work the health chart technology being created by Apple™ and the smart watch devices being developed to interface directly with the program, which truly revolutionizes surgical care in the future.

Since the cloud-based system and method is agnostic to the local device operating systems, the conversion of the menus and images from the mobile doctor devices and HC staff devices and the patient devices can be translated to the Glass™ operating system and other mobile camera—interactive display environments.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The phrase "at least one of A and B" is used herein and/or in the following claims, where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables.

Section: Abbreviations

In the drawings, and sometimes in the specification, reference is made to certain abbreviations. The following Abbreviations Table provides a correspondence between the abbreviations and the item or feature.

| Abbreviations Table | |
|---|---|
| Admin | Administration, sometimes an Admin Layer |
| addr | address - typically an IP address |
| alt. | alternate or optional path or step, see also Opt. for optional |
| API | application program interface |
| app | sometimes App - a small program that calls up another program, sometimes directed to a server |
| appln. | application |
| appt | appointment |
| ASP | application service provider - server on a network |
| bd | board |
| cmd | command |
| comm. | communications, typically telecommunications |
| comp. | computer having internet enabled communications module |
| Cos. | companies |
| CPU | central processing unit |
| cr.cd. | credit card |
| DB | data base |
| dele | delete |
| Displ | display, typically display an interactive page or display screen |
| doc | document |
| drv | drive, e.g., computer hard drive |
| Dr. | doctor, see also HCP for Health Care Professional |
| ds | data storage |
| e | encryption |
| e-fax | an electronic version of a fax document or letter |
| e.g. | for example |
| em | email |
| equip | equipment |
| Fac | Facility, as in Healthcare Facility |
| fnc | function, for example, a "save doc" function |
| GDF | geographically diverse facilities |

-continued

| Abbreviations Table | |
|---|---|
| Geo | geographic location or code (geo.loc. is GPS data) |
| GPS | geo positioning system and location (optionally time data) |
| HC | Health care |
| HCP | health care provider, sometimes also a health care professional |
| HC field | a category or recognized field for health care workers, including doctors and nurses |
| h-link | hyper link to a certain webpage or landing page |
| Hosp | hospital or any other type of healthcare facility such as a clinic, doctor's office, surgical center, etc. |
| I/O | input/output |
| IOS | an Operating System typically for Apple (tm) products |
| id | identify |
| ie or IE | Internet-enabled device, like a smart phone, tablet computer, computer, etc. |
| IP addr. | internet protocol address of internet enabled device |
| loc | location |
| mem | memory |
| mess. | message as in SMS or text message |
| mic | microphone or audio pickup device |
| mkting | marketing |
| ntwk | network, namely a telecomm network, typically internet based network. A local area network is also possible. |
| obj | object, for example, a data object |
| opt | optional or alternative program or module |
| OS | Operating system for a computer-based or processor based device |
| PL | Patient Layer |
| pg. | page, typically a web page, may be a landing web page |
| pgm | program |
| ph | phone, namely an internet enabled phone, such as a smart phone |
| ph.no. | phone number |
| prn | print, as in print screen function |
| proc | processor, typically a microporcessor |
| pt. | point, as in jump point to another portion of the program |
| Pty | party engaged in communications |
| P/W | password |
| pwr | power |
| rcd | database record or record profile or data record, see audio record (a-rcd), voice to text or "V-Text rcd" and keypad generated text data as "K-text rcd" |
| re | regarding or relating to |
| rel | release |
| rem | reminder, such a a reminder email to the HC-W |
| RQT | request |
| rev | review |
| rpt | Report |
| rt | real time, may include day and time stamp data |
| RX | medical drugs or medical equipment |
| sch | schedule |
| sec | security |
| sel | select |
| sig cond | signal conditioner |
| sm-ph | smart phone coupled to the internet via a telecomm |
| smart ph | smart phone coupled to the internet via a telecomm |
| sms | text message |
| spkr | speaker or audio announcement device |
| stmt | statement, as in bank statement, or payment made statement |
| Svr | sever, as in web server |
| Sys | system, typically the cloud based computer server network |
| Sys Op | System Operator |
| t | time |
| telecom | telecommunications system or network |
| tblt | tablet computer |
| txr | transmitter - receiver device, maybe BLUETOOTH (tm), LAN, wireless telecom network, or radio frequency |
| UPP | user's personal profile, for example a patient completes a UPP prior to inputting data about his or her situation |
| URL | Uniform Resource Locator, x pointer, or other network locator |
| univ. | universal application or common application |
| w/ | with |
| w/in | within |
| w/out | without |
| wrt | with respect to |

Section: Description of System and Method Features

The system described above notes that the user has at least one, and sometimes multiple Internet-enabled (IE) devices, such as, smart phone, cell phone with an ap (an access point), tablet computer, computer, or other IE device that is internet enabled. Computer tablets and other electronic devices may be configured in this manner. The app or internet portal permits the person to access the system. If the user communicates with the system in a voice mode, the user interacts primarily with an interactive voice response system or module, an IVR. The IVR translates the voice into text data.

The present invention relates processes data via computer systems, over the Internet and/or on a computer network (LAN or WAN), and computer programs, computer modules and information processing systems accomplish these tracking services.

It is important to know that the embodiments illustrated herein and described herein below are only examples of the many advantageous uses of the innovative teachings set forth herein. In general, statements made in the specification of the present application do not necessarily limit any of the various claimed inventions. Moreover, some statements may apply to some inventive features but not to others. In general, unless otherwise indicated, singular elements may be in the plural and vice versa with no loss of generality. In the drawings, like numerals refer to like parts or features throughout the several views.

The present invention could be produced in hardware or software, or in a combination of hardware and software, and these implementations would be known to one of ordinary skill in the art. The system, or method, according to the inventive principles as disclosed in connection with the preferred embodiment, may be produced in a single computer system having separate elements or means for performing the individual functions or steps described or claimed or one or more elements or means combining the performance of any of the functions or steps disclosed or claimed, or may be arranged in a distributed computer system, interconnected by any suitable means as would be known by one of ordinary skill in the art.

According to the inventive principles as disclosed in connection with the preferred embodiments, the invention and the inventive principles are not limited to any particular kind of computer system but may be used with any general purpose computer, as would be known to one of ordinary skill in the art, arranged to perform the functions described and the method steps described. The operations of such a computer, as described above, may be according to a computer program contained on a medium for use in the operation or control of the computer as would be known to one of ordinary skill in the art. The computer medium which may be used to hold or contain the computer program product, may be a fixture of the computer such as an embedded memory or may be on a transportable medium such as a disk, as would be known to one of ordinary skill in the art. Further, the program, or components or modules thereof, may be downloaded from the Internet of otherwise through a computer network.

The invention is not limited to any particular computer program or logic or language, or instruction but may be practiced with any such suitable program, logic or language, or instructions as would be known to one of ordinary skill in the art. Without limiting the principles of the disclosed invention any such computing system can include, inter alia, at least a computer readable medium allowing a computer to read data, instructions, messages or message packets, and other computer readable information from the computer readable medium. The computer readable medium may include non-volatile memory, such as ROM, flash memory, floppy disk, disk drive memory, CD-ROM, and other permanent storage. Additionally, a computer readable medium may include, for example, volatile storage such as RAM, buffers, cache memory, and network circuits.

Furthermore, the computer readable medium may include computer readable information in a transitory state medium such as a network link and/or a network interface, including a wired network or a wireless network, that allow a computer to read such computer readable information.

Those of skill in the art will appreciate that the various illustrative modules, components, engines, and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules, components, and method steps described in connection with the embodiments disclosed herein can be implemented or performed with hardware such as a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor is hardware and can be a microprocessor, but in the alternative, the processor can be any hardware processor or controller, microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm and the functionality of a component, engine, or module described in connection with the embodiments disclosed herein can be embodied directly in hardware, in software executed by a processor, or in a combination of the two. Software can reside in computer or controller accessible computer-readable storage media including RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a nonexclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

It will be appreciated that embodiments of the invention described herein may be comprised of one or more conventional processors and unique stored program instructions that control the one or more processors to implement, in conjunction with certain non-processor circuits and other elements, some, most, or all of the functions of the powered injector devices described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," "module" and the like as used herein, are defined as a sequence of instructions designed for execution on a computer system. A "program," "software," "application," "computer program," or "software application" or "module" may include a subroutine, a function, a procedure, an object method, an object implementation, an executable application, an applet, a servlet, a source code, an object code, a shared library/dynamic load library and/or other sequence of instructions designed for execution on a computer system.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

The overall layout of the system program is to make it specialty specific, portable/mobile, easy to use, intuitively designed workflow with easy graphic user interface, allow for rich user experience, allow all necessary users to work with the same database to avoid duplication of data and processes, create efficiencies, leverage many of the technologies already inexistence such as the smart phone and wearable devices, enable rich connectivity and interactivity between the patient and the physician, decrease the need for multiple pieces of hardware, simplify the IT setup, decrease costs, decrease training needs, automate tasks, make data accessible in real-time and eliminate the need for multiple different software applications to service an office.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

Although the invention is illustrated and described herein as embodied in methods and systems for healthcare solutions, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for accessing a customized surgical schedule from a highly secure system enabled to acquire, process and produce health care data and service records implemented in a cloud computing network and accessed by a plurality of local devices via one or more communications networks on the Internet, the method comprising:
    said cloud computing network receiving a surgical schedule download request from one local device of said plurality of local devices, said one local device having a first operating system, a memory, a display, a keypad input function and GPS locator, said GPS locator generating location data unique to said local device;
    responsive to said surgical schedule request, said cloud computing network downloading to said one local device:
    (a) health care professional daily schedule data which includes surgical and non-surgical appointments for the health care professional at multiple geographically diverse facilities; and
    (b) command code unique to said first operating system which provides for (i) the acquisition of unique location data representative of the current location of the local device; (ii) the filtering out of non-surgical appointment data from said daily schedule data, (iii) the presentation of only surgical appointments from said daily schedule data on the display of said one local device and (iv) a delete schedule data which is activated subsequent to the presentation of said surgical appointments.

2. The method for accessing a customized surgical schedule as claimed in claim 1 wherein said schedule data includes location data said multiple geographically diverse facilities and wherein the presentation of surgical appointments is a presentation of daily surgical schedule data, and wherein the cloud computing network downloads additional command code to calculate and display on said one or both of (a) a distance between said geographically diverse facilities and said current location data of said one local device; and (b) a time to travel from said current location of said one local device and said geographically diverse facilities, based upon the current location data and the location data said multiple geographically diverse facilities.

3. A method for accessing a customized surgical schedule from a highly secure system enabled to acquire, process and produce health care data and service records implemented in a cloud computing network and accessed by a plurality of local devices via one or more communications networks on the Internet, the method comprising:
    receiving a first request from a first local computing device to download a first surgical schedule download for a first health care professional, said first local device having a first operating system, a memory, a display, a keypad input function and GPS locator, said GPS locator generating location data unique to said local device;
    responsive to said first surgical schedule request, said cloud computing network downloading to said first device: (a) a first health care professional daily schedule data which includes both surgical and non-surgical appointments for the first health care professional at multiple geographically diverse facilities; and (b) first command code unique to said first operating system which provides for (i) the acquisition of unique first location data representative of the current location of the first local device; (ii) the filtering out of non-surgical appointment data from said first daily schedule data, (iii) the presentation of only surgical appointments from said daily schedule data on the display of said first local device and (iv) a delete first schedule data which is activated subsequent to the presentation of said surgical appointment data;
    receiving a second request from a second local computing device to download a second surgical schedule download for a second health care professional, said second device having a second operating system, a memory, a display, a keypad input function and GPS locator, said GPS locator generating location data unique to said second device;
    responsive to said second surgical schedule request, said cloud computing network downloading to said second device: (a) second health care professional daily schedule data which includes surgical and non-surgical appointments for the second health care professional at multiple geographically diverse facilities; and (b) second command code unique to said second operating system which provides for (i) the acquisition of unique second location data representative of the current location of the second device; (ii) the filtering out of non-surgical appointment data from said second daily schedule data, (iii) the presentation of only surgical appointments from said second daily schedule data on the display of said second device and (iv) a second delete schedule data which is activated subsequent to the presentation of said surgical appointment data.

4. A method for accessing a customized surgical schedule from a highly secure system enabled to acquire, process and produce health care data and service records implemented in a cloud computing network and accessed by a plurality of local devices via one or more communications networks on the Internet, the method comprising:
    said cloud computing network receiving a first surgical schedule download request from a first local device of said plurality of local devices, said first local device having a first operating system, a memory, a display, a keypad input function and GPS locator, said GPS locator generating first location data unique to said first device;
    responsive to said first surgical schedule request, said cloud computing network requesting and receiving from said first device the current location of the first device as first current location data;

said cloud computing network:
(a) obtaining previously stored first health care professional daily schedule data which includes surgical and non-surgical appointments for a first health care professional at multiple geographically diverse facilities, said first daily schedule data previously stored in said cloud computing network;
(b) filtering out of non-surgical data from said first daily schedule data, and obtaining only surgical appointments from said first daily schedule data as first surgical schedule data;

said cloud computing network downloading the first surgical daily schedule data to said first local device and downloading commands (i) to enable the presentation of the first surgical daily schedule data on the display of said first device and (ii) prohibit one or the other of a save function for said first surgical daily schedule data in said first device or a print screen function during the presentation of first surgical daily schedule data.

5. A method for accessing a customized surgical schedule from a highly secure system enabled to acquire, process and produce health care data and service records implemented in a cloud computing network and accessed by a plurality of local devices via one or more communications networks on the Internet, the method comprising:

receiving a first request from a first local computing device to download a first surgical schedule download for a first health care professional, said first local device having a first operating system, a memory, a display, a keypad input function and GPS locator, said GPS locator generating location data unique to said first local device;

responsive to said first surgical schedule request, said cloud computing network requesting and receiving from said first device the current location of the first device as first current location data;

said cloud computing network: (a) obtaining previously stored first health care professional daily schedule data which includes surgical and non-surgical appointments for a first health care professional at multiple geographically diverse facilities, said first daily schedule data previously stored in said cloud computing network; (b) filtering out first non-surgical appointment data from said first daily schedule data, and obtaining only surgical appointments from said first daily schedule data as first surgical schedule data;

downloading the first surgical daily schedule data to said first local device and downloading first commands (i) to enable the presentation of the first surgical daily schedule data on the display of said first device and (ii) prohibit one or the other of a save function for said first surgical daily schedule data in said first device or a print screen function during the presentation of first surgical daily schedule data;

receiving a second request from a second local computing device to download a second surgical schedule download for a second health care professional, said second local device having a second operating system which is different than said first operating system, said second local device having a memory, a display, a keypad input function and GPS locator, said GPS locator generating location data unique to said second local device;

responsive to said second surgical schedule request, said cloud computing network requesting and receiving from said second device the current location of the second device as second current location data;

said cloud computing network: (a) obtaining previously stored second health care professional daily schedule data which includes surgical and non-surgical appointments for a second health care professional at multiple geographically diverse facilities, said second daily schedule data previously stored in said cloud computing network; (b) filtering out second non-surgical data from said second daily schedule data, and obtaining only surgical appointments from said second daily schedule data as second surgical schedule data;

downloading the second surgical daily schedule data to said second local device and downloading second commands (i) to enable the presentation of the second surgical daily schedule data on the display of said second device and (ii) prohibit one or the other of a save function for said second surgical daily schedule data in said second device or a print screen function during the presentation of second surgical daily schedule data.

* * * * *